US012740861B2

(12) United States Patent
Gloss et al.

(10) Patent No.: US 12,740,861 B2
(45) Date of Patent: Sep. 22, 2026

(54) TENSION MEMBER ROUTING ELEMENTS IN TRANSCATHETER STENTED PROSTHESIS TENSIONING SYSTEM

(71) Applicant: Medtronic, Inc., Minneapolis, MN (US)

(72) Inventors: Michael Gloss, Minneapolis, MN (US); Patrick Griffin, Galway (IE); Paul Rothstein, Elk River, MN (US); Jeffrey Sandstrom, Scandia, MN (US); Brendan Vaughan, Miltown Malbay (IE); Stephen Montgomery, Galway (IE); Alan McGuinn, Granmore (IE)

(73) Assignee: MEDTRONIC, INC., Minneapolis, MN (US)

(*) Notice: Subject to any disclaimer, the term of this patent is extended or adjusted under 35 U.S.C. 154(b) by 884 days.

(21) Appl. No.: 18/094,090

(22) Filed: Jan. 6, 2023

(65) Prior Publication Data

US 2023/0145819 A1 May 11, 2023

Related U.S. Application Data

(63) Continuation of application No. 16/911,480, filed on Jun. 25, 2020, now Pat. No. 11,571,302, which is a (Continued)

(51) Int. Cl.

| | |
|---|---|
| ***A61F 2/24*** | (2006.01) |
| ***A61F 2/95*** | (2013.01) |
| *A61F 2/966* | (2013.01) |

(52) U.S. Cl.

CPC .......... *A61F 2/2436* (2013.01); *A61F 2/2439* (2013.01); *A61F 2/95* (2013.01);

(Continued)

(58) Field of Classification Search

CPC ....................... A61F 2002/9511; A61F 2/2439

See application file for complete search history.

(56) References Cited

U.S. PATENT DOCUMENTS 4,157,777 A 6/1979 Tomasch
4,768,507 A 9/1988 Fischell et al.

(Continued)

FOREIGN PATENT DOCUMENTS

CA 2339133 A1 2/2000
CN 201664353 U 12/2010

(Continued)

OTHER PUBLICATIONS

International Search Report and Written Opinion in PCT/US2018/029777, mailed Oct. 22, 2018, 5 pages.

(Continued)

*Primary Examiner* — Alvin J Stewart

(74) *Attorney, Agent, or Firm* — Wentsler LLC

(57) ABSTRACT

The disclosure relates to transcatheter stented prosthesis delivery devices including transition elements that route, constrain, support and reduce damage to tension member wear as tension in the tension members is varied to adjust the compression of a stented prosthesis loaded onto the delivery device. Various disclosed tension elements include inserts, edge treatments and guides proximate a distal portion of the delivery device upon which the stented prosthesis is loaded. In some embodiments, the transition feature is positioned proximate a location where at least one tension member transitions from a first orientation that is not parallel to the distal portion to a second orientation that is generally parallel to the distal portion. Further embodiments disclose configurations and methods of selectively locking and (Continued)

unlocking a longitudinal and/or rotational position of the stent frame with respect to the distal portion of the delivery device.

10 Claims, 23 Drawing Sheets

Related U.S. Application Data continuation of application No. 15/964,438, filed on Apr. 27, 2018, now Pat. No. 10,743,990.

(60) Provisional application No. 62/490,896, filed on Apr. 27, 2017.

(52) U.S. Cl.
CPC ..... *A61F 2/2418* (2013.01); *A61F 2002/9511* (2013.01); *A61F 2/9522* (2020.05); *A61F 2002/9665* (2013.01); *A61F 2210/0014* (2013.01)

(56) References Cited

U.S. PATENT DOCUMENTS

| | | | |
|---|---|---|---|
| 6,344,042 B1 | 2/2002 | Curtis et al. | |
| 10,420,642 B2 * | 9/2019 | Gloss | A61F 2/2433 |
| 10,772,749 B2 * | 9/2020 | Gloss | A61F 2/95 |
| 11,638,585 B2 * | 5/2023 | Thornton | A61F 2/90 623/1.15 |
| 12,458,495 B2 * | 11/2025 | Rothstein | A61F 2/2439 |
| 2004/0167547 A1 | 8/2004 | Beane et al. | |
| 2005/0033323 A1 | 2/2005 | Kim | |
| 2005/0119722 A1 | 6/2005 | Styrc et al. | |
| 2006/0178725 A1 | 8/2006 | Cornelius | |
| 2008/0255656 A1 | 10/2008 | Saeed | |
| 2009/0048656 A1 | 2/2009 | Wen | |
| 2010/0274187 A1 | 10/2010 | Argentine | |
| 2012/0277734 A1 * | 11/2012 | Goetz | A61F 2/95 606/1 |
| 2014/0018906 A1 | 1/2014 | Rafiee | |
| 2014/0148895 A1 * | 5/2014 | King | A61F 2/07 623/1.13 |
| 2014/0155937 A1 | 6/2014 | Shinde | |
| 2014/0257454 A1 | 9/2014 | McGee | |
| 2015/0250481 A1 | 9/2015 | Chobotov | |
| 2017/0348099 A1 * | 12/2017 | Mendelson | A61F 2/2439 |
| 2018/0116839 A1 * | 5/2018 | McHugo | A61F 2/962 |
| 2018/0242968 A1 | 8/2018 | Mirochinik et al. | |
| 2018/0311042 A1 | 11/2018 | Gloss et al. | |
| 2019/0015206 A1 * | 1/2019 | McGuinn | A61F 2/95 |
| 2019/0125534 A1 * | 5/2019 | Arcaro | A61F 2/2436 |
| 2019/0231568 A1 * | 8/2019 | Garcia | A61F 2/954 |
| 2022/0287831 A1 * | 9/2022 | Thornton | A61B 17/12109 |
| 2023/0190445 A1 * | 6/2023 | Collins | A61F 2/07 623/1.11 |
| 2024/0091008 A1 * | 3/2024 | McGuinn | A61F 2/95 |

FOREIGN PATENT DOCUMENTS

| | | | |
|---|---|---|---|
| CN | 102548486 | A | 7/2012 |
| CN | 102858275 | A | 1/2013 |
| CN | 202740158 | U | 2/2013 |
| CN | 103200900 | A | 7/2013 |
| CN | 103860292 | A | 6/2014 |
| CN | 104135973 | A | 11/2014 |
| CN | 204600795 | U | 9/2015 |
| CN | 105188612 | | 12/2015 |
| CN | 105726163 | A | 7/2016 |
| EP | 1006939 | A1 | 6/2000 |
| EP | 2745813 | A1 | 6/2014 |
| ES | 2296854 | T3 | 5/2008 |
| FR | 2366090 | A1 | 4/1978 |
| WO | 9301768 | A1 | 2/1993 |
| WO | 2009137359 | A1 | 11/2009 |
| WO | 2011011481 | A2 | 1/2011 |
| WO | 2011133792 | A1 | 10/2011 |
| WO | 2012033604 | A2 | 3/2012 |
| WO | 2012068175 | | 5/2012 |
| WO | 2013096411 | A1 | 6/2013 |
| WO | 2013118352 | A1 | 8/2013 |
| WO | 2016109738 | A2 | 7/2016 |

OTHER PUBLICATIONS

Supplementary search report from counterpart Chinese Patent Application No. 201880028027.8, dated May 24, 2022, with English translation.

Transcatheter Technologies GmbH, Tumbao-Endovascular Aortic Repair, https://www.youtube.com/watch?v=tac54aPN9Uc, Jan. 14, 2015.

M. Leon, "Newcomers and Important Design Concepts: TAVR in the Future," Columbia University Medical Center Cardiovascular Research Foundation, Transcatheter Valve Therapies TVT, Jun. 15-18, 2016.

* cited by examiner 50
40
32
33
1760
1722
1738

50
40
32
1760
1838
1822
1839

1850
40
32
1760
1822
33
1838
1839

TENSION MEMBER ROUTING ELEMENTS IN TRANSCATHETER STENTED PROSTHESIS TENSIONING SYSTEM

CROSS-REFERENCE TO RELATED APPLICATIONS

This application is a continuation of U.S. application Ser. No. 16/911,480, filed Jun. 25, 2020, which is a continuation of U.S. application Ser. No. 15/964,438, filed Apr. 27, 2018, now U.S. Pat. No. 10,743,990, which claims the benefit of U.S. Provisional Patent Application No. 62/490,896, filed Apr. 27, 2017, the entire contents of which are incorporated herein by reference.

BACKGROUND

The disclosure relates to transcatheter stented prosthesis delivery devices or systems that utilize one or more elongate tension members to compressively retain a stented prosthesis to the delivery device.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The present disclosure addresses problems and limitations associated with the related art.

SUMMARY

The present disclosure relates to numerous delivery devices or systems for transcatheter stented prosthesis (e.g., stented prosthetic heart valve) loading, delivery and implantation. Such delivery devices can include an optional outer delivery sheath assembly, a shaft assembly and a handle assembly. The delivery device provides a loaded delivery state in which the stented prosthesis is loaded and compressed over a distal portion of the shaft assembly. Compression of the stented prosthesis can be adjusted with one or more elongate tension members, which extend around the stented prosthesis and proximately to an actuation and release assembly that can optionally be located in the handle assembly. The delivery device can be manipulated to adjust tension in the tension members to permit the stented prosthesis to self-expand, contract and ultimately release from the shaft assembly.

Partial or full compression of the stented prosthesis can be achieved by pulling or otherwise retracting the tension members proximally. The present inventors have observed that with some tension member routing configurations, the tension member experiences wear and damage at a location where the tension member transitions from a first orientation that is generally parallel to the distal portion (e.g., as the tension member is routed back to the handle assembly) to a second orientation that is not parallel to the distal portion (e.g., extending from the stented prosthesis) or vice versa. In order to protect the tension members from abrasion and wear as tension in the tension member is adjusted, the disclosed embodiments can include one or more transition elements that create a smooth, rounded transition surface for the tension members to travel over as they change direction. After the tension members are released from the stented prosthesis, via various methods, the delivery device can be withdrawn from the patient.

Various disclosed embodiments are configured so that a longitudinal and/or rotational position of at least one end of a stent frame of the stented prosthesis is locked or maintained with respect to the delivery device. By locking the longitudinal and/or rotational position of at least one end or location of the stent frame, more predictable positioning and more equal and uniform crimping of the stent frame can be achieved. By locking the rotational position of the distal portion of the delivery device to the stent frame, clocking of the stented prosthesis for anatomical rotational alignment may be achieved more efficiently with minimal backlash. Locking can be achieved, for example, with a suture, wire, or the like interconnecting one end of the stent frame to the distal portion of the delivery device.

Aspects of the disclosure relate to a combination of a stented prosthesis loaded to a delivery device. The combination comprises a stented prosthesis including a stent frame having a compressed arrangement and an expanded arrangement; wherein the stent frame includes a distal end and a proximal end and an aperture provided at the distal end. The combination further includes a delivery device having a distal portion on which the stented prosthesis is loaded. The delivery device includes a release member extending along the distal portion. The combination also includes a lock member threaded through the aperture and engaged with the release member; wherein the lock member restricts longitudinal and/or rotational movement of the stent frame with respect to the distal portion of the delivery device when the stent frame is in both of the compressed arrangement and the expanded arrangement until release of the lock member from the release member.

Aspects of the disclosure relate to a method comprising providing a combination including: a stented prosthesis including a stent frame having a compressed arrangement and an expanded arrangement; wherein the stent frame includes a distal end and a proximal end and an aperture provided at one or more ends, e.g., the distal end. The method further includes providing a delivery device including a distal portion on which the stented prosthesis is loaded in the compressed arrangement. The delivery device further includes a release member extending along the distal portion and a lock member threaded through the aperture. The method further comprises delivering the stented prosthesis to a target site and disengaging the release member from the lock member to unlock the lock member so that the stent frame can move longitudinally and rotate with respect to the distal portion of the delivery device in the compressed arrangement. In some methods, the lock also prevents rotational movement of the stented prosthesis with respect to the distal portion of the delivery device.

Additional embodiments include a delivery device for delivering a stented prosthesis to a target site. The delivery device comprises an elongate tension member that can compressively retain the stented prosthesis to the delivery device; and a shaft assembly having a distal portion configured to retain the stented prosthesis. The shaft assembly further including a transition element secured to the distal portion, the transition element at least partially defining a lumen; wherein the elongate tension member extends in a first direction distally along a length of the distal portion, the elongate tension member is then routed through the lumen and then extends in a second direction that is different than the first direction. The transition element provides a rounded surface over which the tension member contacts as the tension member extends from the first direction to the second direction.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
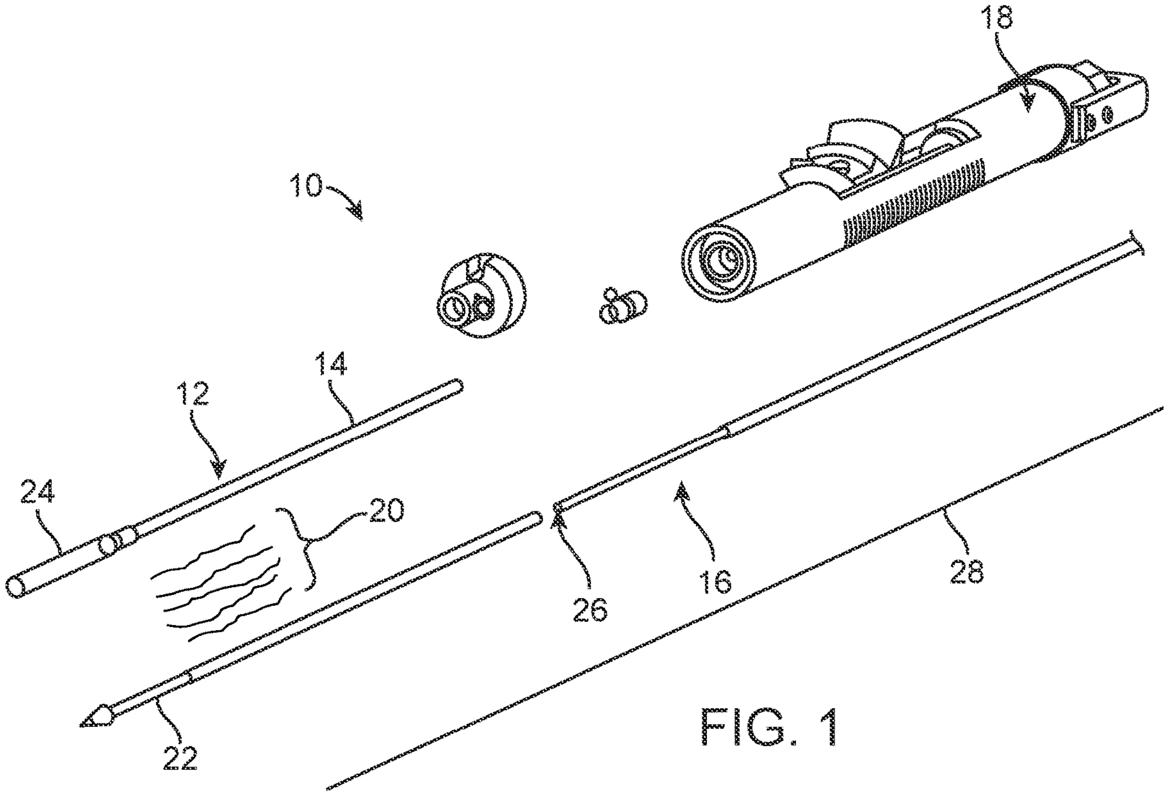
FIG. 1 is a perspective view of an example of a delivery device or system for delivering a stented prosthetic heart valve.
Figure 2A:
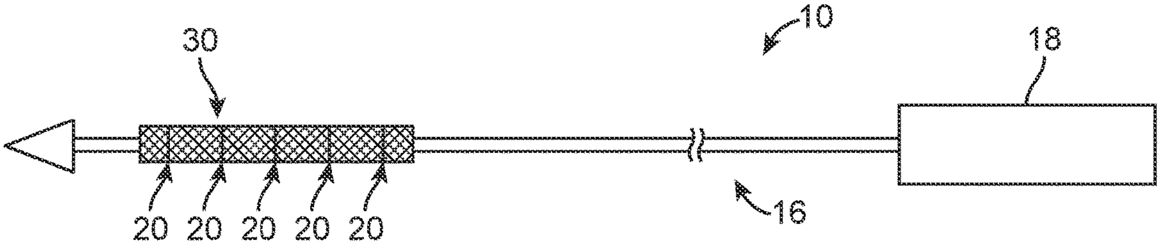
FIG. 2A is a schematic illustration of the delivery device of FIG. 1 having the stented prosthetic heart valve positioned over a distal portion of the delivery device with a plurality of elongate tension members in a compressed arrangement.
Figure 2B:
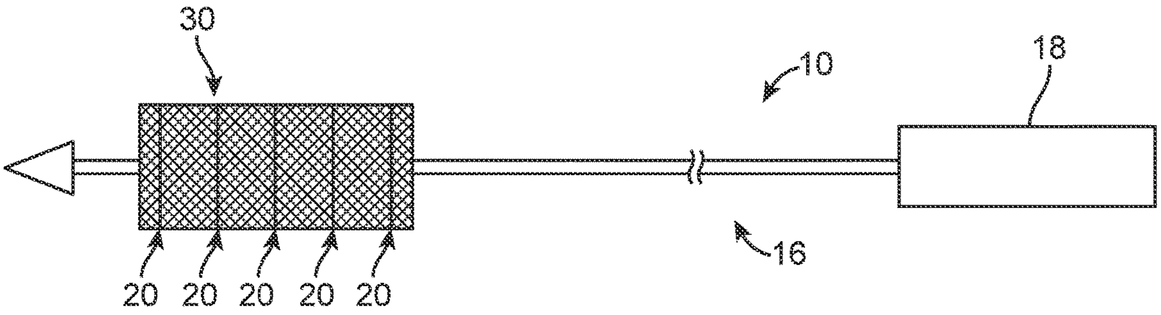
FIG. 2B is a partial, schematic illustration of the delivery device of FIG. 2A having the stented prosthetic heart valve positioned over the distal portion; the stented prosthetic heart valve shown in an expanded arrangement.
Figure 3:
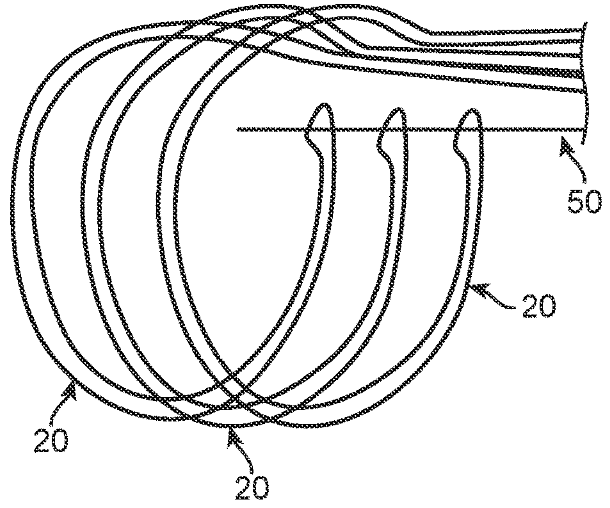
FIG. 3 is a schematic illustration of how three elongate tension members can be releasably positioned around a stented prosthesis with a release pin and tension in the tension members can be adjusted with a single actuator (the stented prosthesis is omitted for ease of illustration).

As described below, some aspects of the present disclosure relate to delivery devices or systems utilizing one or more tension members to compress and retain a stented prosthesis to the delivery device during transcatheter delivery to a target site. By way of background, general components of one non-limiting example of a delivery device 10 with which some aspects of the present disclosure are useful are illustrated in FIGS. 1-3. The delivery device 10 is arranged and configured for percutaneously delivering a stented prosthesis, such as a stented prosthetic heart valve 30 (schematically illustrated), to a target site. The delivery device 10 includes an optional outer sheath assembly 12 having a flexible outer sheath 14, a flexible shaft assembly 16 and a handle assembly 18. The shaft assembly 16 can include a distal portion 22 and define a continuous lumen 26 (referenced generally) sized to slidably receive an auxiliary component such as a guide wire 28. In this embodiment, the outer sheath 14 is interconnected to a capsule 24 that is selectively disposed over the stented prosthesis 30 and assists in constraining the stented prosthesis 30 in the compressed arrangement. The capsule 24 can be retracted by the handle assembly 18 to expose the stented prosthesis 30 for deployment.

One or more tension members 20 (e.g., sutures, cords, wires or filaments) are further provided, and can be considered part of the delivery device 10 in some embodiments or as part of the stented prosthesis 30 in other embodiments. It is to be understood that the terms "tension member", "suture", "cord", "wire" and filament", as used herein, should be considered equivalent, interchangeable elements. Some examples in which the tension members 20 can be arranged are schematically illustrated in FIGS. 2A-3 (the stented prosthesis and other delivery device components being omitted in FIG. 3 for ease of illustration). One end of each of the tension members 20 can be secured proximate the handle assembly 18, then each tension member 20 can extend distally to wrap around the stented prosthesis 30 positioned over the distal portion 22 to a release pin 50 positioned adjacent the stented prosthesis 30 and then back to the handle assembly 18 or other mechanism for maintaining and adjusting the desired level of tension in the tension members 20 either individually or in pairs or groups of tension members. Due to friction losses as the tension member 20 goes around the stent frame 32, positioning the release pin 50 approximately 360 degrees from the distal portion 22 results in asymmetric crimping and consequently the stent frame in-folding. Therefore, in some embodiments, the release pin 50 is placed 180 degrees from the distal portion 22, but for practical purposes is more practically placed within the distal portion 22, or about 360 degrees from the distal portion 22. The release pin 50 is optional, with the primary benefit being a reduced length of the tension member(s) 20 to adjust compression of the stented prosthesis 30, and may be omitted as in the embodiments of FIGS. 20-21. Other tension member arrangements are envisioned. The delivery device 10 provides a loaded, compressed arrangement (FIG. 2A) in which the stented prosthesis 30 is loaded over the shaft assembly 16 and is compressively retained on the distal portion 22 by the tension members 20. As is schematically illustrated in FIGS. 2A-2B, compression of the stented prosthesis 30 is adjustable with the tension members 20. In this illustrated embodiment, the tension members 20 wrap around the stented prosthesis 30 normal to an axis of the shaft assembly 16. Alternatively, the tension members 20 can be configured to wrap around the stented prosthesis 30 at other angles with respect to the axis of the shaft assembly 16. The present inventors have found that wrapping the tension members 20 at an angle to the distal portion 22 creates non-symmetric crimping of the stented prosthesis 30, which causes in-folding of the stent frame 32. In-folding of the stent frame 32 can decrease structural integrity.

After being loaded, compressed and optionally sheathed with the capsule 24, the stented prosthesis 30 is delivered to the native defective heart valve. Once the stented prosthesis 30 is sheathed with the capsule 24, tension in the tension members 20 can be released, if desired to release tension in the tension members 20 for more effective steering and a more flexible shaft assembly 16, as the capsule 24 maintains the stented prosthesis 30 in the compressed arrangement. Once in position, the capsule 24 is retracted (if provided) and/or tension in the tension members 20 is lessened or released to permit the stented prosthesis 30 to self-expand to an expanded arrangement, partially releasing and ultimately fully deploying the stented prosthesis 30 from the shaft assembly 16 (see, FIG. 2B). Then, the release pin 50 is proximally retracted to disengage from the tension members 20 so that the tension members 20 can be released from the stented prosthesis 30 and withdrawn from the patient along with the delivery device 10. In alternate embodiments, the release pin 50 is omitted and the tension members 20 can be cut for release from the stented prosthesis 30, as with the embodiments of FIGS. 20-21. If the stented prosthesis 30 is longitudinally and/or rotationally locked to the distal portion 22 as discussed in greater detail below, the lock may be released prior to tension member 20 release, after tension member release, simultaneous with tension member release, or if tension members are released individually, it may be unlocked at any point in the sequence. The present disclosure focuses on numerous ways to configure a delivery device, such as the delivery device 10, to prevent wear of the tension member 20 as tension in the tension member(s) is adjusted. It is to be understood that the delivery device 10 disclosed above is provided as only one example and that aspects of the disclosure can also be used with other types of delivery devices.

As referred to herein, the stented prostheses and stented prosthetic heart valves or "prosthetic valves" useful with the various devices and methods of the present disclosure may assume a wide variety of configurations. The prosthetic valves can include a bioprosthetic heart valve having tissue leaflets or a synthetic heart valve having polymeric, metallic or tissue-engineered leaflets, and can be specifically configured for replacing valves of the human heart. The stented prosthesis and prosthetic valves of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

Figure 4A:
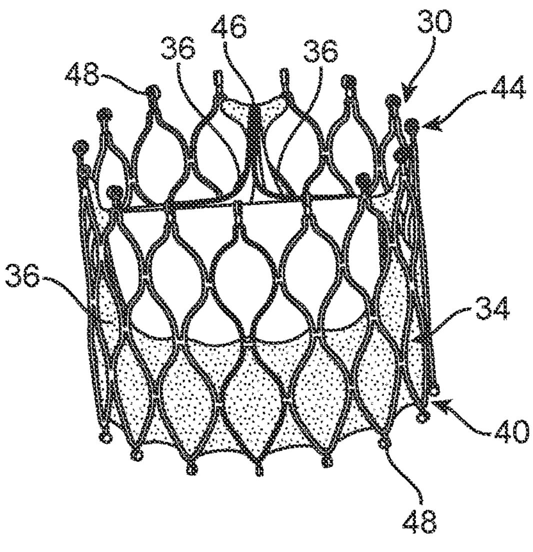
FIG. 4A is a perspective view of one stented prosthetic heart valve that can be used with the delivery devices disclosed herein shown in the expanded arrangement.
Figure 4B:
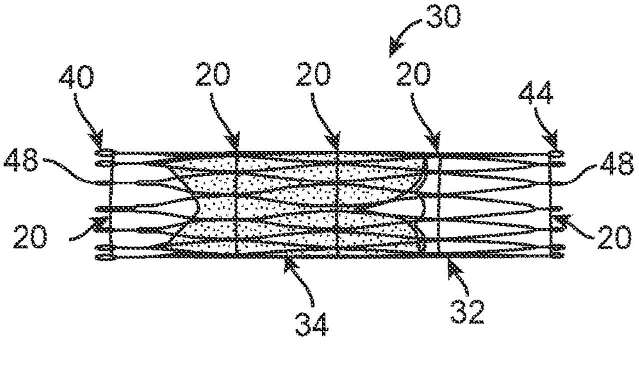
FIG. 4B is a front view of the stented prosthesis of FIG. 4A in the compressed arrangement.

One non-limiting example of the stented prosthesis 30 is illustrated in detail in FIGS. 4A-4B. As a point of reference, the stented prosthesis 30 is shown in a normal or expanded arrangement in the view of FIG. 4A and a compressed arrangement in FIG. 4B. The stented prosthesis 30 includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the stented prosthesis 30 can be achieved with one or more tension members 20.

The valve structure 34 of the stented prosthesis 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 4A-4B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The stented prosthesis 30 includes a first end (inflow) 40 and an opposing second end (outflow) 44 of the stented prosthesis 30. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around the stent frame 32 (only one post 46 is clearly visible in FIG. 4A).

Figure 5A:
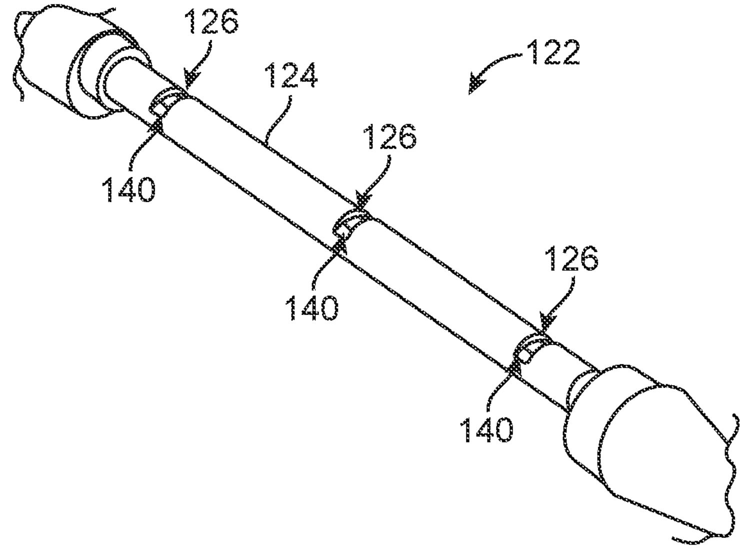
FIG. 5A is a perspective view of a distal portion of a delivery device, such as the delivery device of FIG. 1.
Figure 5B:
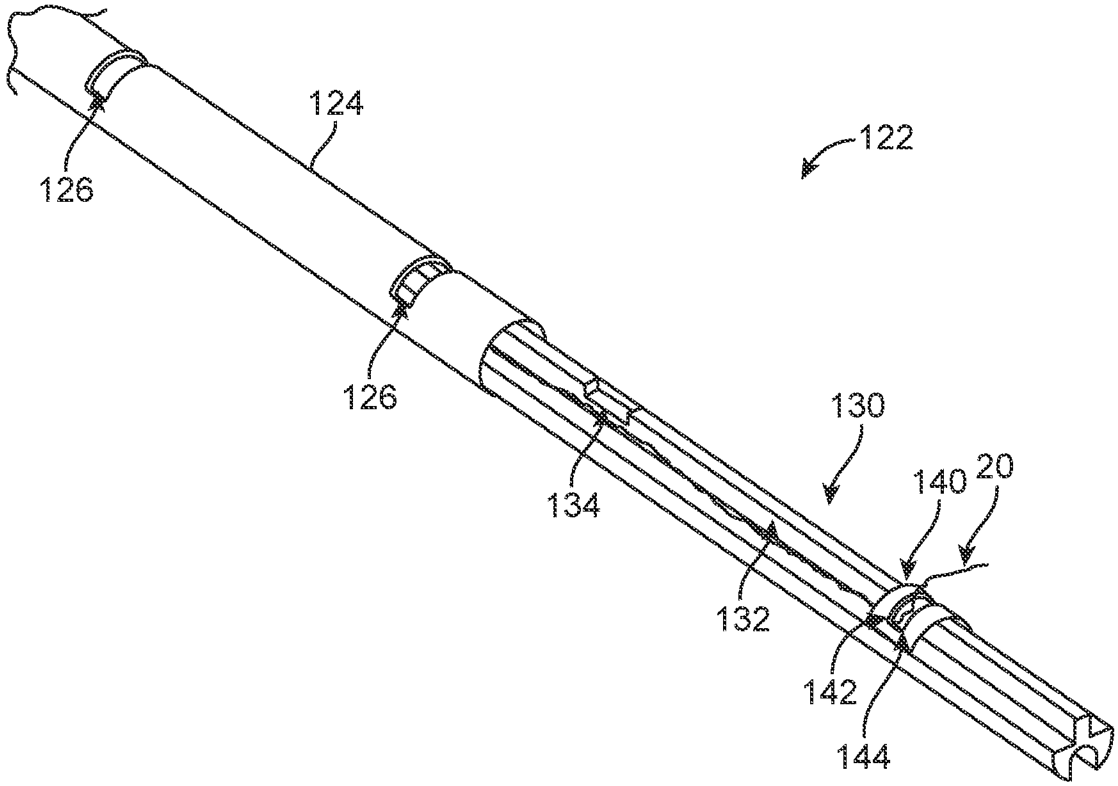
FIG. 5B is a partial, partially-exploded view of the distal portion of FIG. 5A.

Turning now also to FIGS. 5A-5B, which illustrate one example embodiment of a distal portion 122 that can be used in replacement of the distal portion 22 of FIG. 1 or with another device. In this embodiment, the distal portion 122 includes a hollow cylindrical body 124 having a plurality of windows 126. Within the hollow cylindrical body 124 is an insert 130 including a ridge 132. The ridge 132 may include a plurality of notches 134 that are aligned with each of the windows 126 when the insert 130 is operatively positioned within the distal portion 122. Positioned over each of the notches 134 is a transition element 140. In operation, one or more tension members 20 extend around the prosthetic valve and through one window 126, transition element 140, and also through the notch 134 and along the insert 130 proximally to a handle assembly or the like (only one example tension member 20 is shown for ease of illustration in FIG. 5B). The transition element 140 provides a smooth, rounded surface for the tension members 20 to travel over as tension in the respective tension member(s) 20 is adjusted to compress and release compression of the stented prosthesis. When tension in the tension members 20 is adjusted, the length of tension member 20 around the stented prosthesis changes. Transition surfaces along a path as the tension member(s) 20 changes direction and travels through the window 126 and the notch 134 and then along the insert 130, within the distal portion 122 can cause damage to the tension member(s) 20. The transition element 140 includes an aperture 142 defined by a beveled, rounded or otherwise smooth surface 144 for the tension member(s) 20 to travel over to reduce wear of the tension member(s) 20.

Figure 6A:
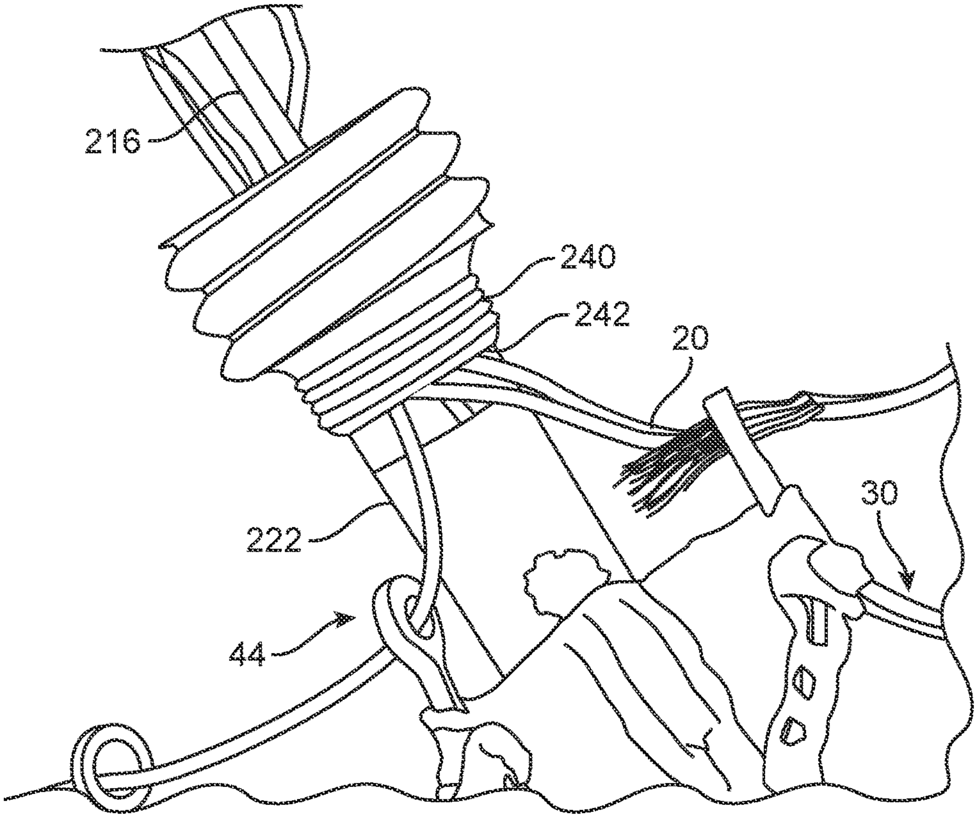
FIG. 6A is a partial plan view of a portion of an alternate delivery device, similar to that of FIG. 1.
Figure 6B:
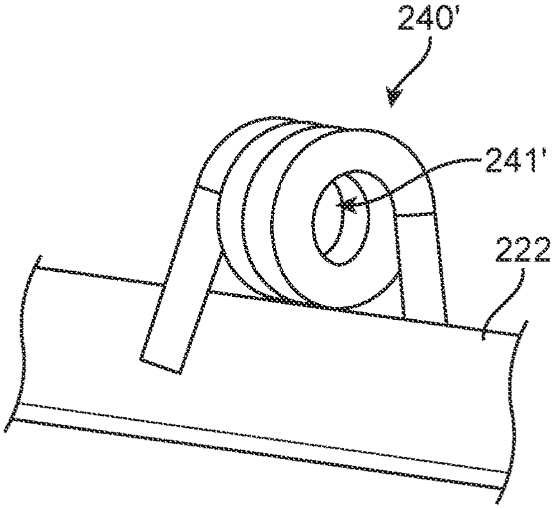
FIG. 6B a partial, perspective view of an alternate embodiment of a transition element secured to a distal portion.
Figure 6C:
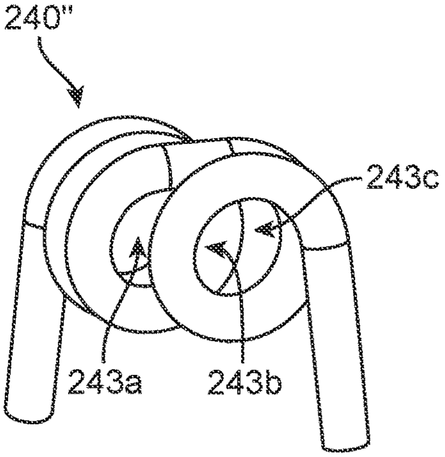
FIG. 6C is a perspective view of an alternate embodiment of a transition element.

Referring now also to FIG. 6A, which illustrates an alternate transition element 240 that can be used with a distal portion 222 of a delivery device, such as the delivery device 10 of FIG. 1. In this embodiment, the transition element 240 is a coil having a smooth, rounded outer surface 242 over which one or more transition member(s) 20 pass over as they are redirected from the stented prosthesis 30 proximally along a shaft assembly 216 to a handle assembly or the like (e.g., see also, the shaft assembly 16 and the handle assembly 18 of FIG. 1). The tension members 20 can be any of the type disclosed herein. Alternatively, in the embodiment of FIG. 6B the tension members (not shown) can be routed through a transition element 240' being a coil forming a lumen 241' that is joined to the exterior of the distal portion 222. The coil can be a single coil 240' (FIG. 6B), or a pair of coils 240" (FIG. 6C) to keep a plurality of tension members separated. By overlapping two coils, three lumens 243*a-c* are present and each lumen 243*a-c* may be used to constrain a release pin (e.g., 50) or tension member (e.g., 20), as desired.

Figure 7A:
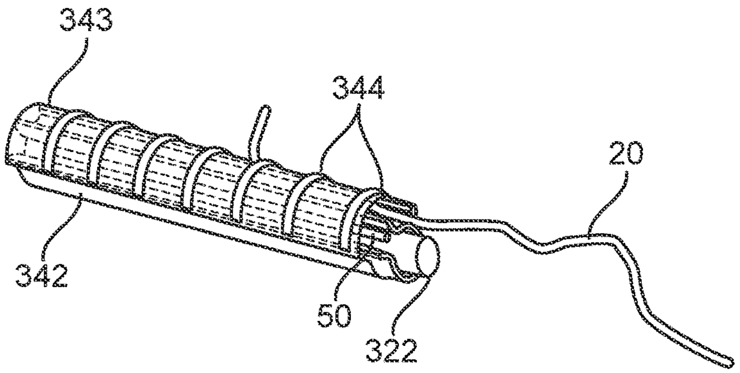
FIGS. 7A-7D collectively illustrate portions of an alternate distal portion.
Figure 7B:
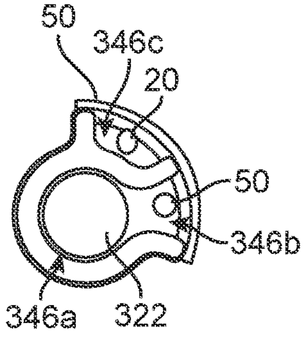
Figure 7C:
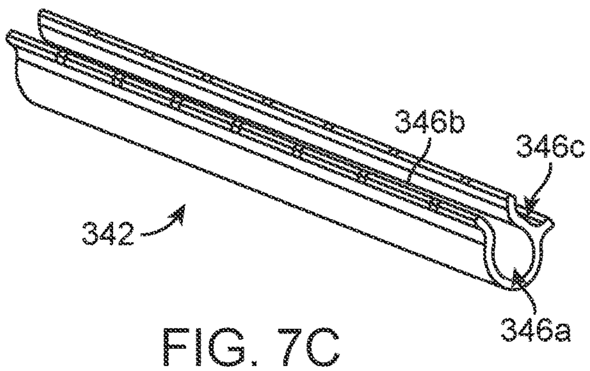
Figure 7D:
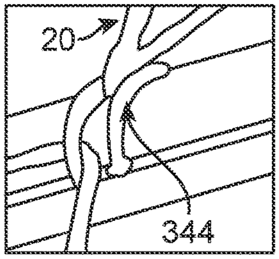

Referring now also to FIGS. 7A-7D, which illustrate alternate components that can be used with any of the embodiments disclosed herein. This embodiment includes a distal portion 322 (which could be substituted for distal portion 22, for example) including a sleeve 342, optional shield 343 and cage members 344 (generally referenced) that are welded or otherwise attached and extend around at least a portion of a circumference of the distal portion 322 on the sleeve 342. In some embodiments, the cage members 344 extend around the entirety of the sleeve 342. As best shown in FIG. 7B, the sleeve 342 defines three channels 346*a-c*. The distal portion 322 extends through the first channel 346*a*, a release pin 50, as described above, can extend through the second channel 346*b* and one or more tension members (not shown, see also the prior disclosed embodiments) can be routed through the third channel 346*c*. The cage members 344 are configured to provide an atraumatic surface 348 for one or more tension members 20 to travel across as they are redirected from the stented prosthesis to a location proximal the stented prosthesis through the third channel 346*c*. The shield 343, if provided, has windows (not visible) through which the tension members 20 can be routed. The shield 343 may keep blood, valve frame, or valve leaflets from interacting with the tension members 20. The sleeve 342 can take many other configurations.

Figure 7E:
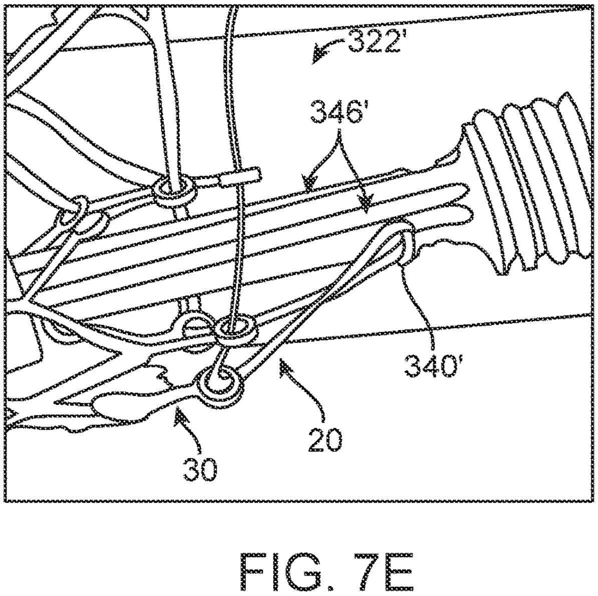
FIG. 7E illustrate yet another distal portion having a plurality of channels arranged in a generally spiral orientation.

Referring now also to FIG. 7E, which illustrates yet another distal portion 322' that can be used in replacement of the distal portion 22 of FIG. 1 or with another device. The distal portion 322' can retain prosthesis 30 with at least one tension member 20 (only one tension member 20 is visible). The distal portion 322' of this embodiment includes a plurality of channels 346' (e.g., eight channels) similar to the concept shown in FIGS. 7A-7D; however the channels 346' align the individual tension members 20 arms with a similar number (eight) transition elements 340' (only one is shown) having an atraumatic surface over which one or more tension members 20 can travel over as the tension member 20 changes direction. In some embodiments, as shown, the channels 346' can be oriented in a generally spiral orientation on the distal portion 322' with respect to a central axis of the distal portion 322'. In one embodiment, the tension members 20 are symmetrically spaced around a central guide wire lumen (not shown) in the distal portion 322'. On the distal portion 322' is beneficial to redirect some of the tension members 20 close to 180 degrees from the transition element(s) 340' and spiral-configured channels 346' are one way of bringing the tension members 20 around an outer circumference of the distal portion 322'.

Figure 8A:
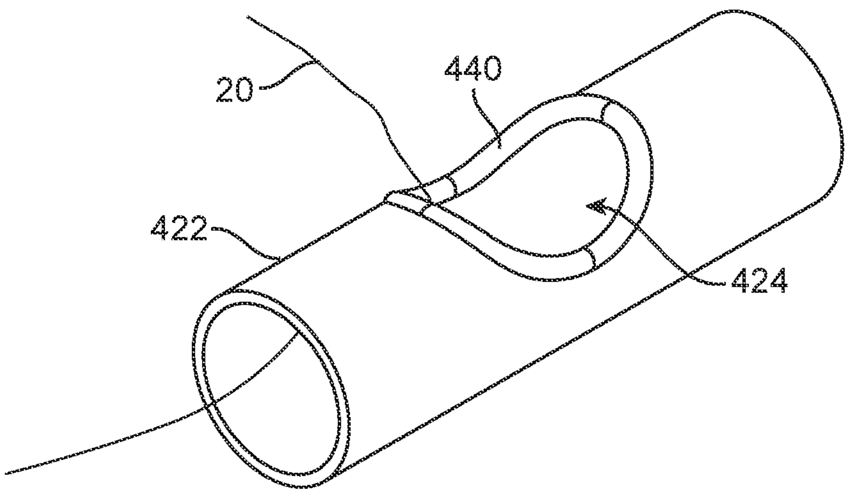
FIG. 8A is a schematic illustration of a truncated distal portion having a transition element.
Figure 8B:
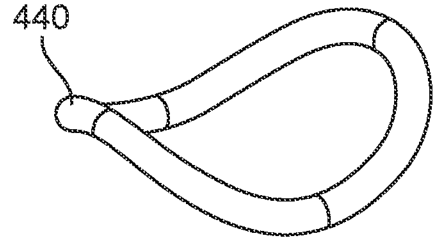
FIG. 8B is a perspective view of the transition element of FIG. 8A.

Referring now also to FIGS. 8A-8B, which illustrate a section of an alternate distal portion 422 that can be used in replacement of the distal portion 22 of FIG. 1 or with another device. In this embodiment, the distal portion 422 can include one or more apertures 424 (only one aperture is shown in a truncated section of the distal portion) through which one or more tension members 20 are routed. The aperture 424 includes a transition element 440 being a ring, made of wire or the like that has a smooth rounded surface to provide abrasion relief as the tension member(s) 20 passes over the ring 440. In one example embodiment, the ring 440 is a C-shaped wire formed and welded to a metal laser cut hypotube forming the distal portion 422. In the illustrated embodiment, the ring 440 is hyperbolic paraboloid shape. Any additional apertures for routing one or more tension members 20 into the distal portion 422 can be similarly configured, as desired.

Figure 9:
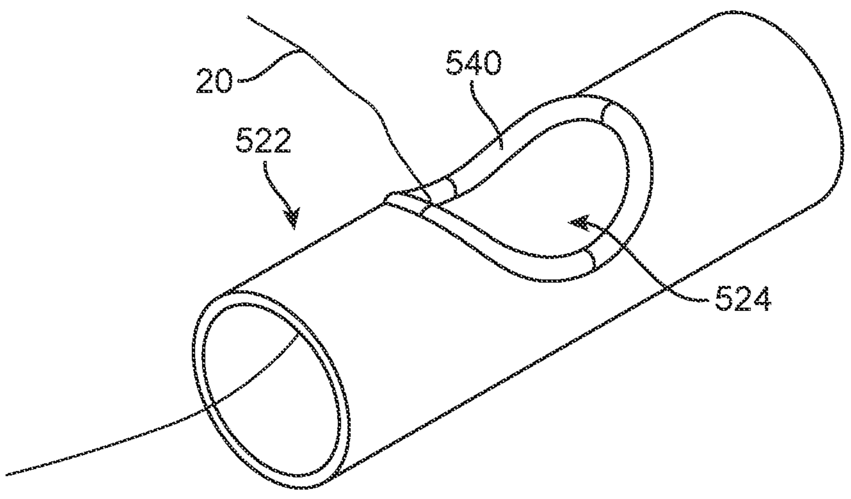
FIG. 9 is a schematic illustration of a truncated distal portion having an alternate transition element.

Referring now also to FIG. 9, which illustrates part of an alternate distal portion 522 that can be used in replacement of the distal portion 22 of FIG. 1 or with another device. In this embodiment, the distal portion 522 can include one or more apertures 524 (only one is shown) through which one or more tension members 20 are routed. The aperture 524 includes a transition element 540 being an electroplated edge, which has a smooth, rounded surface to provide abrasion relief as the tension member(s) 20 pass over the edge 540 to change direction. Any additional apertures for routing one or more tension members into the distal portion 522 can be similarly configured, as desired.

Figure 10:
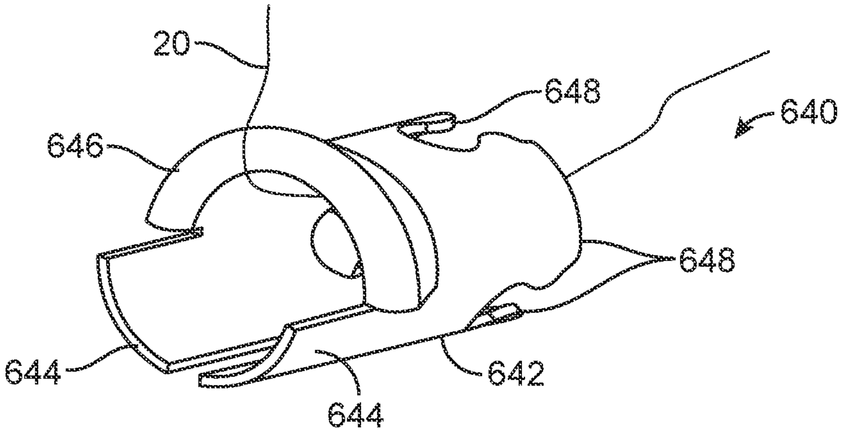
FIG. 10 is a perspective view of an alternate transition element.

Referring now also to FIG. 10, which discloses an alternate transition element 640 that can be inserted into any aperture of and secured coaxially with any of the distal portions disclosed herein to create a smooth, rounded surface for one or more tension members 20 to travel over as the tension members 20 pass from outside of the distal portion to within the distal portion. In this embodiment, the transition element 640 includes a generally cylindrical body 642 having one or more flanges 644 and a lip 646. When the transition element 640 is operatively positioned within an aperture of a distal portion (see also, FIG. 8A and related disclosure), the lip 646 is configured to extend from within the distal portion, through the aperture and around an edge of the aperture. The lip 646 can, in some embodiments, define an arc that extends about 180 degrees with respect to a center axis of the body 642. As desired, the body 642 can include a plurality of features 648 to assist in maintaining the transition element 640 in place within the aperture of the distal portion.

Figure 11:
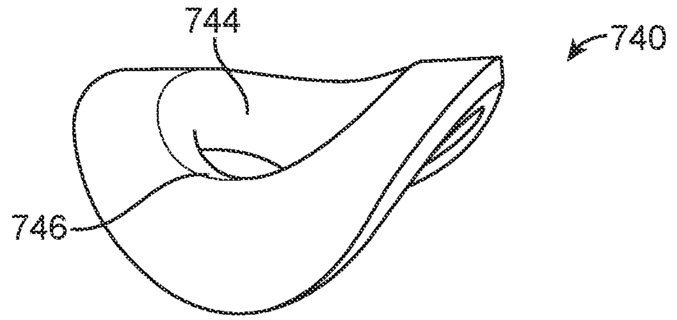
FIG. 11 is a perspective view of yet another transition element.

Referring now also to FIG. 11, which illustrates an alternate transition element 740. The transition element 740 defines an aperture 742 having a smooth, rounded edge 744. The transition element 740 is configured to be secured and maintained within one of the apertures of the distal portion (similar to what is shown in FIG. 8A or, alternatively, any distal portion disclosed herein) to effectively cover the edge of the aperture of the distal portion. In this embodiment, the transition element 740 is arranged on the distal portion so that the aperture 742 is aligned with the aperture in the distal portion. Similar to other disclosed embodiments, one or more tension members can be routed over the smooth rounded edge 744 as the one or more tension members pass from outside of the distal portion to within the distal portion.

Figure 12:
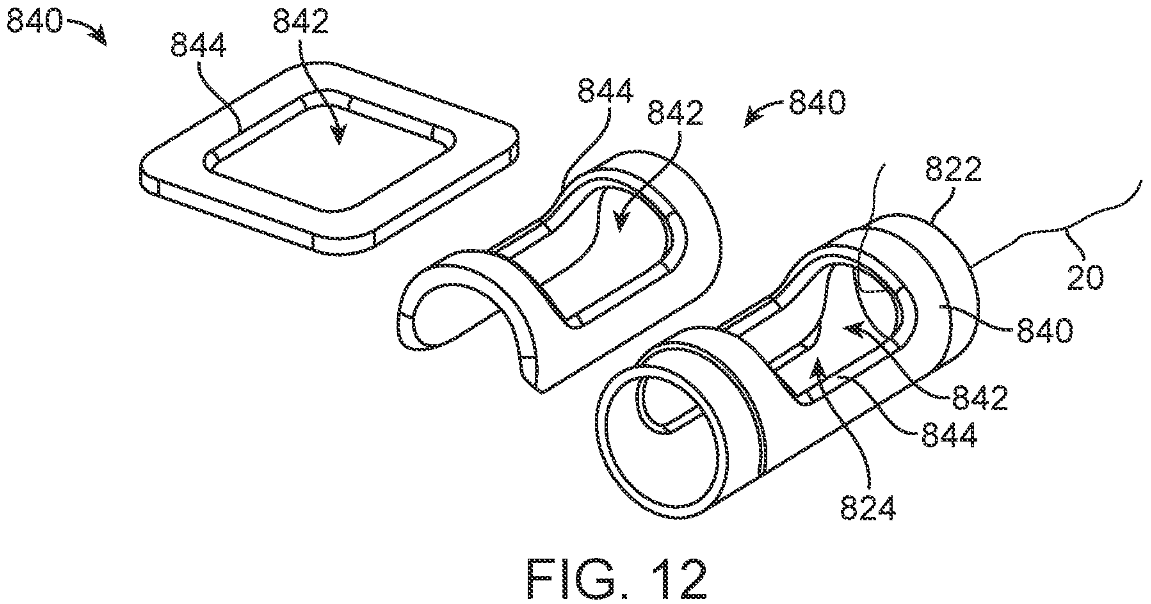
FIG. 12 illustrates a series of steps for forming a transition element and assembling the transition element to a distal portion.

Now also referring to FIG. 12, which illustrates an alternate transition element 840 in multiple stages of formation and assembly to a distal portion 822 (shown as truncated for ease of illustration). In this embodiment, the transition element 840 includes an aperture 842 that can be positioned to align with an aperture 824 in the distal portion 822, which can be used in replacement of the distal portion 22 of FIG. 1 or with another device. The transition element 840 further includes a beveled, rounded, smooth edge 844 around the aperture 842 to provide an atraumatic surface for one or more tension members 20 to travel across. The edge 844 can be coined or otherwise machined, for example, within a flat metal blank that is subsequently bent to conform to the curvature of the distal portion 822. In various embodiments, upon assembly, the transition element 840 can have an outer diameter that is larger than an outer diameter of the distal portion 822 and the transition element 840 can have an inner diameter that is slightly smaller than an inner diameter of the distal portion 822.

Figure 13:
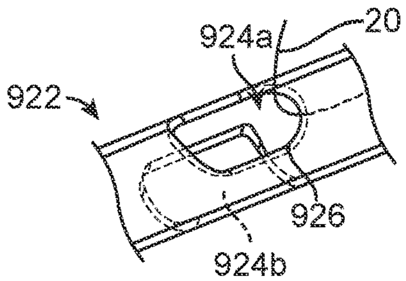
FIG. 13 is a perspective view of a distal portion having a transition element (the distal portion shown as partially transparent).

Referring now also to FIG. 13, which illustrates an alternate distal portion 922 (shown as truncated and partially transparent) configuration in which an aperture 924*a* in the distal portion 922 that receives one or more tension members 20 is manufactured to have a transition element 926 being a beveled, rounded, smooth edge that is coined or otherwise integrally formed into the distal portion 922. The distal portion 922 can be used in replacement of the distal portion 22 of FIG. 1 or with another device. The transition element 926 can be formed, for example, by inserting tooling through the aperture 924*a* such that the tooling is positioned about 180 degrees from the aperture 924*a*. As illustrated, the distal portion 922 can include two opposing apertures 924*a*, 924*b*. The second aperture 924*b* can also include a coined edge 926 or the like, as desired. One purpose of aperture 924*b* is to allow access of a laser beam, polishing element, or cutting tool to smooth the edges of the aperture 924*a*.

Figure 14A:
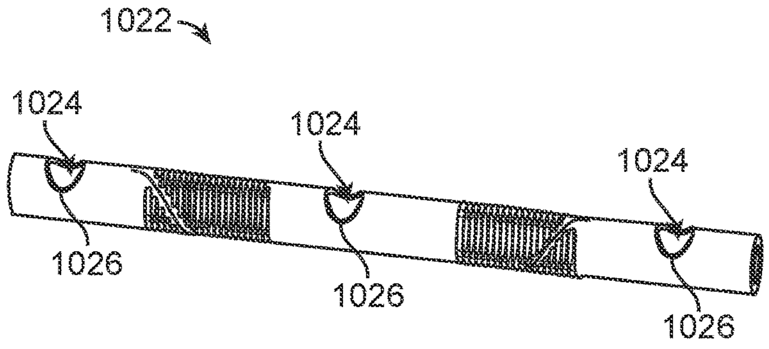
FIG. 14A is a perspective view of an alternate distal portion having a plurality of transition elements.
Figure 14B:
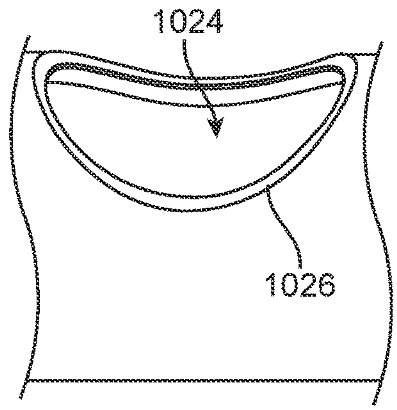
FIG. 14B is an enlarged section of a portion of the distal portion of FIG. 14A.
Figure 14C:
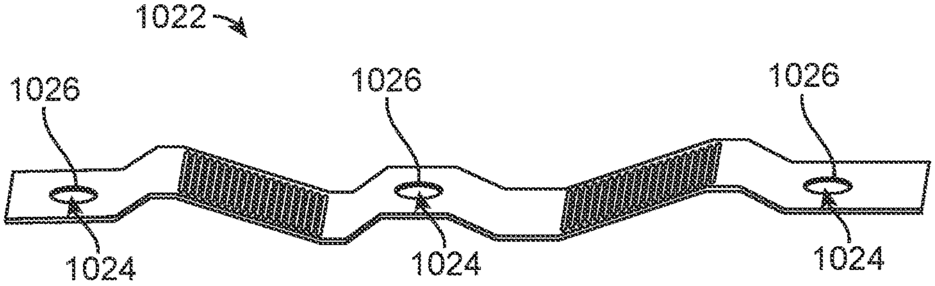
FIG. 14C is a perspective view of the distal portion prior to rolling the distal portion into the shape of FIG. 14A.

Turning now also to FIGS. 14A-14C, which illustrate an alternate distal portion 1022 that can be used in replacement of the distal portion 22 of FIG. 1 or with another device. The distal portion 1022 has a plurality of apertures 1024, each having a transition element 1026, which is a smooth, coined edge. As with prior disclosed embodiments, the transition element 1026 provides an atraumatic surface over which one or more tension members (not shown) can pass as the tension member(s) is redirected from the stented prosthesis (not shown), through the aperture 1024, inside and along the distal portion 1022. The distal portion 1022 of this embodiment can optionally be formed from a sheet of material as is generally illustrated in FIG. 14C that is subsequently rolled and seam welded to produce the distal portion 1022 configuration shown in FIG. 14A.

Figure 15:
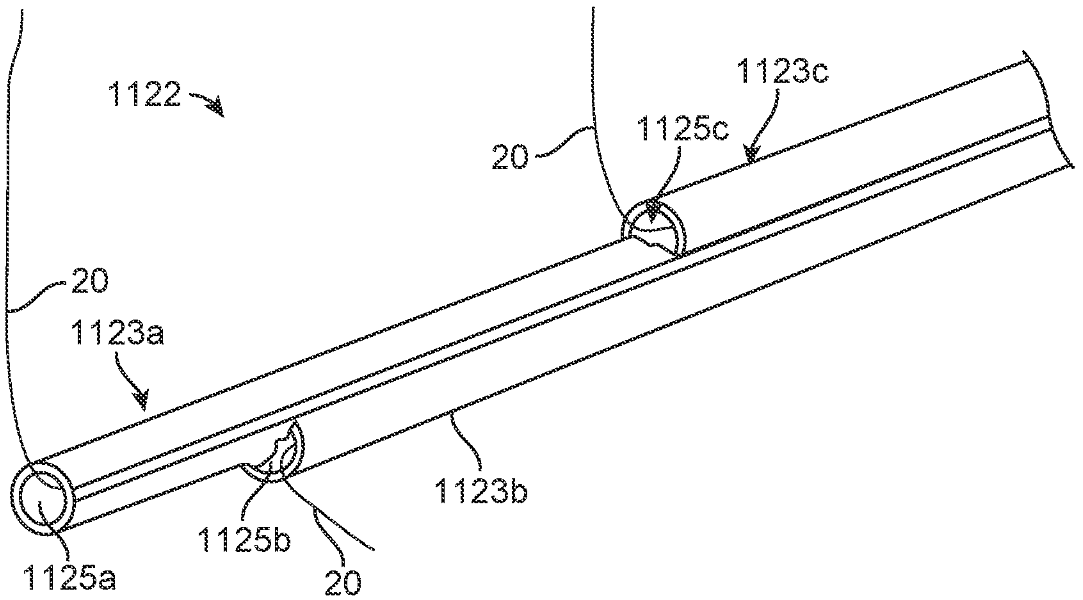
FIG. 15 is a perspective view of an alternate distal portion having three tiers.

Now also referring to FIG. 15, which illustrates an alternate distal portion 1122 that can be used in replacement of the distal portion 22 of FIG. 1 or with another device. The distal portion 1122 includes three tiers 1123*a-c*, each defining a lumen 1125*a-c* extending along a length of the distal portion 1122. The first tier 1123*a* is the longest, the tier section 1123*b* shorter than the first tier 1123*a* and the third tier 1123*c* is the shortest of the three tiers 1123*a-c*. As illustrated, the varying length of the tiers 1123*a-c* provides staggered points for tension members 20 to exit and enter the respective tiers 1123*a-c*. In this way, the tension members 20 are spaced along a length of the stented prosthesis (omitted) positioned on the distal portion 1122. This distal portion 1122 has a reduced diameter in a region proximate the first and second sections 1123*a-b* where a paravalvular leakage prevention wrap of the stented prosthesis, of the type frequently provided with stented prosthetic heart valves, would be positioned, if provided.

Figure 16:
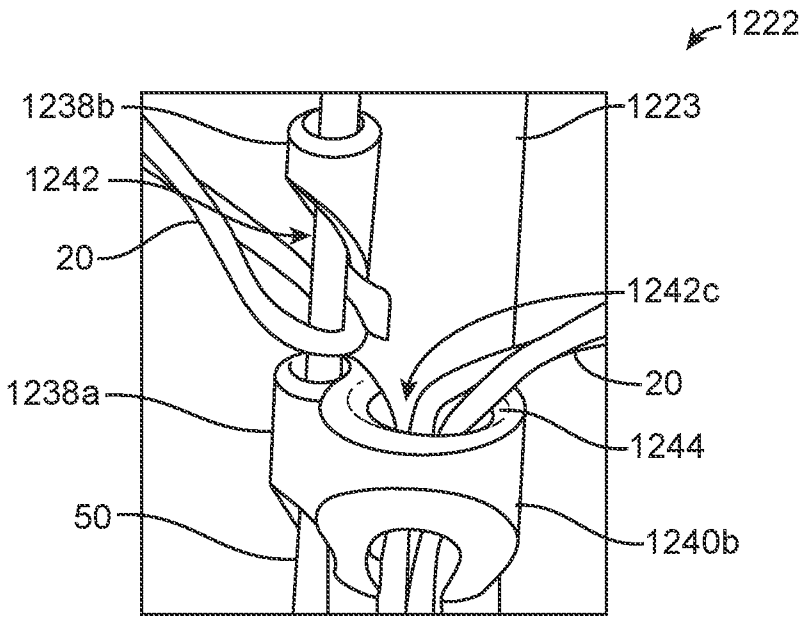
FIG. 16 is a partial, front view of an alternate distal portion.

Referring now also to FIG. 16, which illustrates yet another distal portion 1222 that can be used in replacement of the distal portion 22 of FIG. 1 or with another device. The distal portion 1222 of this embodiment routes at least one tension member 20 and the release pin 50 outside and over a cylindrical body 1223 of the distal portion 1222. In this embodiment, the distal portion 1222 includes guides 1238*a-b* and also one or more transition elements 1240. The first and second guides 1138*a-b* retain the release pin 50 and the transition element 1240 retains at least one tension member 20 and provides an atraumatic, rounded surface 1144 as the tension member 20 changes direction, thus reducing wear and damage to the tension member(s) 20. The distal portion 1222 can include multiple guides 1138*a-b* and/or transition elements 1240, similarly or differently configured, as desired, along a length or circumference of the body 1123.

Figure 17A:
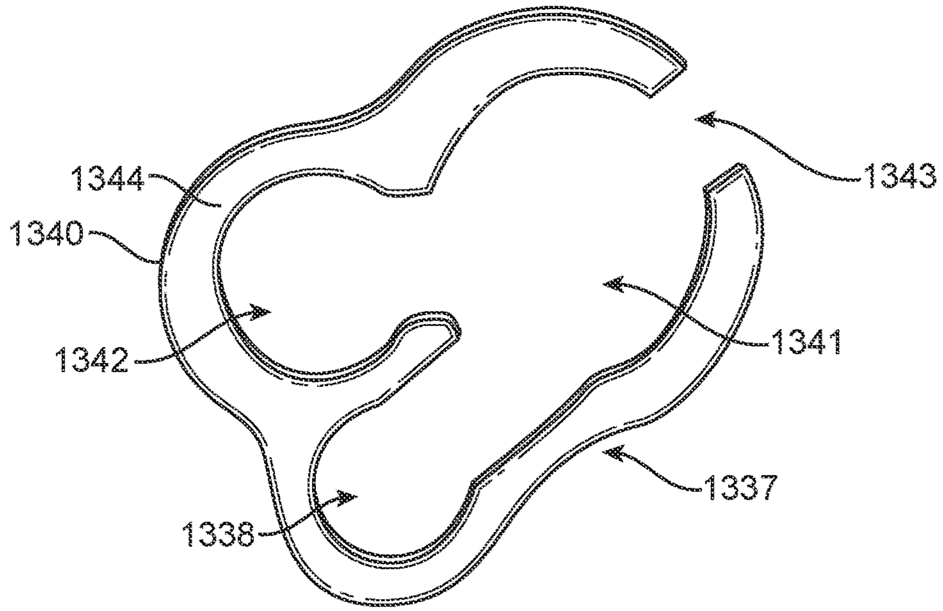
FIG. 17A is a perspective view of an alternate transition element.
Figure 17B:
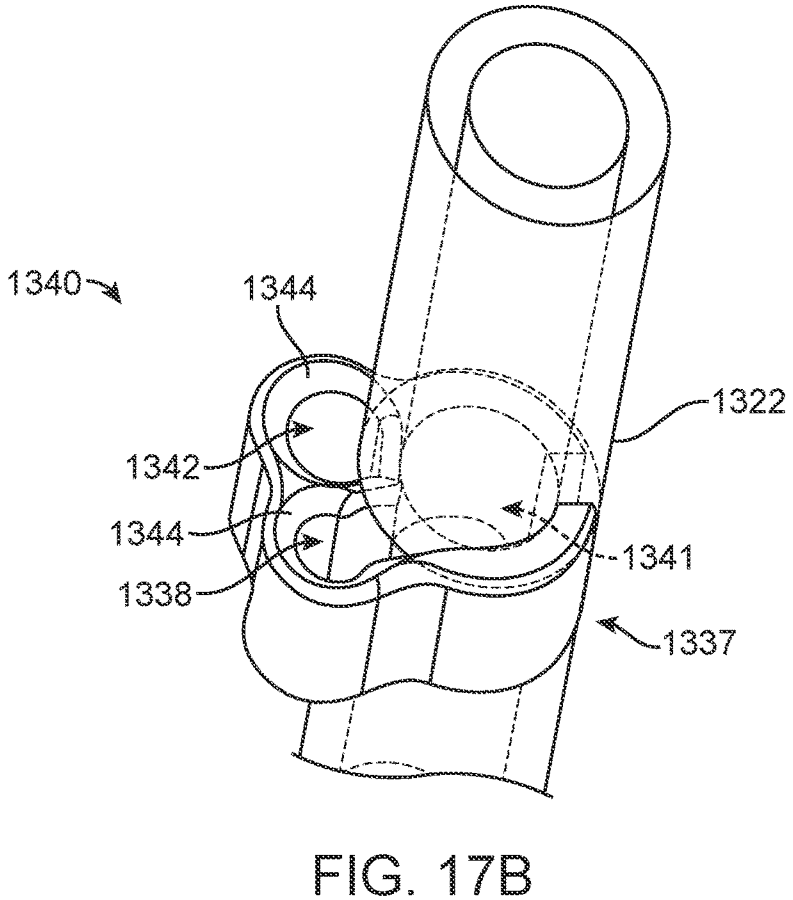
FIG. 17B is a perspective view of a distal portion including the transition element of FIG. 17A.

Turning now also to FIGS. 17A-17B, which collectively illustrate an attachment 1337 that can be operatively secured to a distal portion 1322 (or distal portion 22, for example) to provide a guide 1338, a transition element 1340, as well as a receiving channel 1341 through which the distal portion 1322 is inserted. In this embodiment, a release pin (not shown, see the release pin 50 disclosed above with respect to other embodiments) can be positioned within the guide 1338 and one or more elongate tension members can be routed through apertures 1342 and/or 1338 in the transition element 1340. As with prior disclosed embodiments, the transition element 1340 is configured to have a beveled, rounded surface or edge 1344 proximate the apertures 1342 and or 1338 so that wear of the tension member is reduced. In various embodiments, the rounded, atraumatic edge 1344 is machined into the transition element 1340 or manufactured or machined as a separate component and then welded or otherwise attached proximate the aperture 1342. Alternatively, the atraumatic edge 1344 can be formed by stamping, coining, extruding, honing, electropolishing, acid etching, autogenous welding or the like. Optionally, the attachment 1337 can be clipped, slid or otherwise secured around a distal portion 1322 (see, FIG. 17B). If the attachment 1337 is to be clipped onto the distal portion 1322, the attachment 1337 includes a gap 1343 and is made of a material that provides sufficient flexing such that the gap 1343 can be widened to allow the distal portion 1322 to be inserted therethrough. The distal portion 1322 can include a plurality of similarly configured attachments 1337 along a length of the distal portion 1322, as desired. In various embodiments, the distal portion 1322 includes slots (not shown) for receiving each attachment 1337 so that the profile of the delivery device is minimized by at least somewhat accommodating for the profile increase attributable to the attachment 1337.

Figure 18:
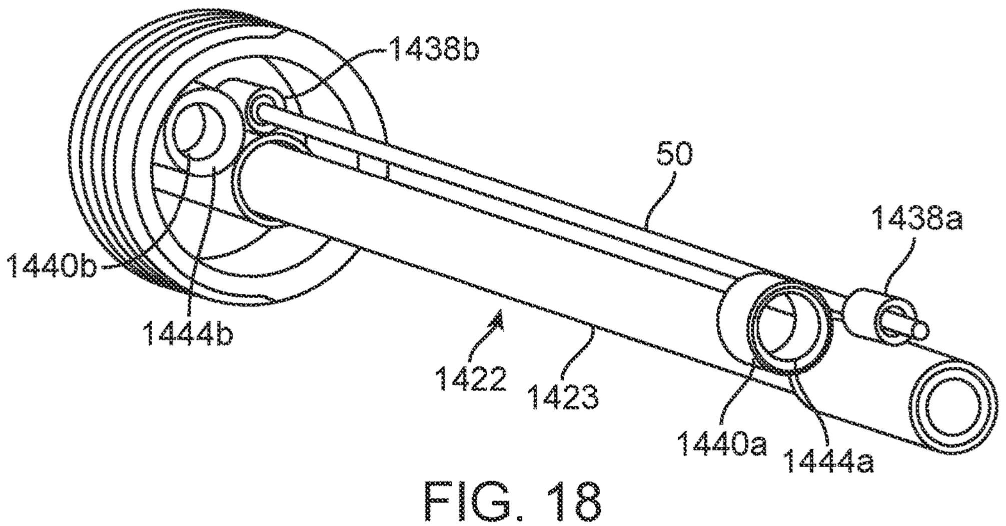
FIG. 18 is a perspective view of an alternate distal portion including a plurality of transition elements.

Referring now also to FIG. 18, which illustrates select components of a distal end of an alternate delivery device, which can be similar to that of FIG. 1 except as explicitly stated. The device includes a distal portion 1422 (which could replace distal portion 22 of FIG. 1) over which a stented prosthesis, such as those disclosed herein, can be loaded. The delivery device can further include the release pin 50 positioned within one or more guides 1438*a-b* located on a cylindrical body 1423 of the distal portion 1422. Also provided are two transition elements 1440*a-b* that each include beveled, rounded surface 1444*a-b* over which one or more tension members (not shown) pass to change directions as the tension member(s) is routed, for example, from the stented prosthesis and along a length of the distal portion 1422. The release pin 50 could alternatively or additionally function as a lock member, as discussed below with respect to other embodiments (see, e.g., FIG. 22 and related disclosure). The guides 1438*a-b* and/or transition elements 1440*a-b* can comprise a machined cylinder or ceramic disc (not visible), which can optionally additionally provide radiolucent properties. The atraumatic, rounded surface 1444*a-b* of the transition elements 1440*a-b* can be machined or formed into the respective transition element 1440*a-b*, which provides abrasion relief for tension members routed therethrough (e.g., in the illustrated embodiment, for tension members positioned at ends of the stent frame).

Figure 19A:
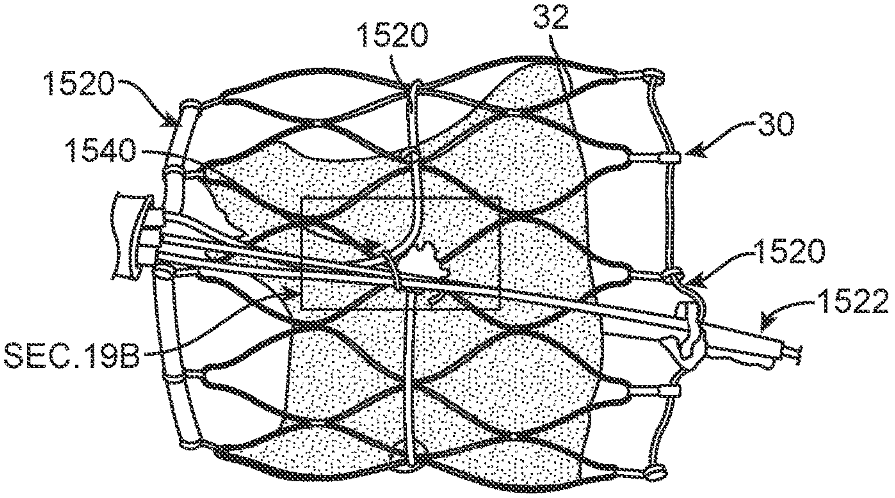
FIG. 19A is a side view of the stented prosthesis positioned over a distal portion; wherein a tension member circumscribing the stented prosthesis is routed through a transition element.
Figure 19B:
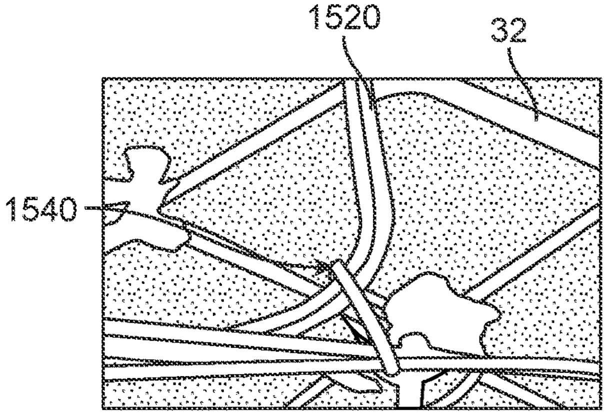
FIG. 19B is an enlarged view of Sec. 19B of FIG. 19A.
Figure 19C:
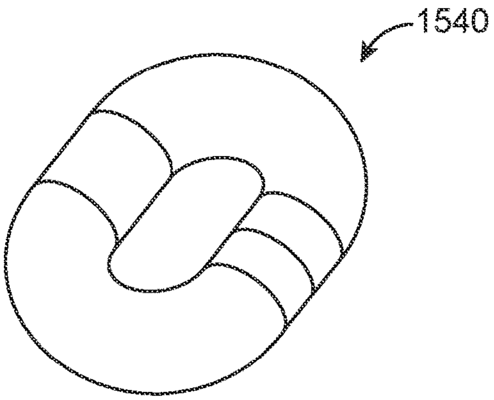
FIG. 19C is a perspective view of the transition element of FIGS. 19A-19B.

A transition element 1540 can also be provided in a delivery device (e.g., such as that of FIG. 1) proximate one or more tension elements 1520 wrapped around the middle or waist of the prosthetic valve as is generally shown in FIGS. 19A-19B. The tension elements 1520 are of the type as disclosed with respect to the tension elements 20 disclosed herein. The transition element 1540 is a ring that redirects and reduces wear on waist tension member 1520 at the point where the tension member 1520 is redirected from the stent frame 32 to along a distal portion 1542 of a delivery device (see also, FIG. 1, for example of on suitable delivery device). The transition element 1540 can include a rigid ring (shown in FIG. 19C) or a flexible loop of material or the like, for example. In some embodiments, the transition element 1540 will be made of the same material as the tension members 1520. The transition element 1540 can be provided in combination with or as a substitute for any of the transition elements disclosed herein, as desired.

Figure 20:
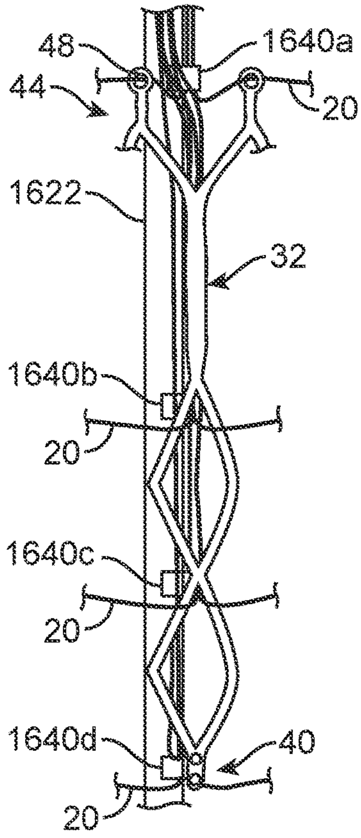
FIG. 20 is a partial, schematic illustration of one way in which tension members can be internally routed around a stent frame of the stented prosthesis relative to a delivery device.

Now also referring to FIG. 20, which illustrates one way in which elongate tension members 20 can be routed in which tension members 20 proximate a middle of the stent frame 32 (partially shown) are generally positioned through or interior to the stent frame 32. A distal portion 1622 over which the stent frame 32 is positioned can include one or more transition elements 1640*a-d* having an atraumatic, rounded surface for the tension members 20 to pass over as they change direction from a direction generally parallel to the distal portion 1622 to a direction generally perpendicular to the distal portion or vice versa. The transition elements 1640*a-d* can be any of the type disclosed herein. Moreover, the distal portion 1622 can be configured substantially similar to the distal portions disclosed above and can be used with the delivery device of FIG. 1, for example.

Figure 21:
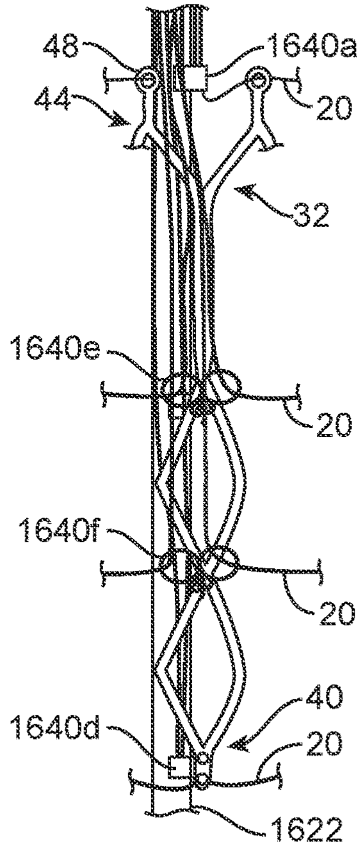
FIG. 21 is a partial, schematic illustration of another way in which tension members can be externally routed around the stent frame relative to the delivery device.

Alternatively, the tension members 20 can be routed exterior to the stent frame 32 (partially shown) as is shown FIG. 21. In such embodiments, it is beneficial for the stent frame 32 to include transition elements 1640*d-e* though which waist tension members 20 can be routed in placed of the transition elements 1640*b-c* of FIG. 20. The transition elements 1640 can be made of a flexible material, such as the material of the tension members 20 and provide an atraumatic surface for one respective tension member 20 to pass through as the tension member 20 transitions from a direction generally parallel to the distal portion 1622 to a direction generally perpendicular to the distal portion 1622 or vice versa.

In addition, it can be beneficial for one end 40 (i.e. distal end) of the stent frame 32 to be longitudinally and/or rotationally locked in position relative to the distal portion 1622. Locking one end 40 of the stent frame 32 is beneficial as the forces on the tension members 20 proximate the middle of the stent frame 32 during expansion of the stent frame 32 will pull the stent frame 32 proximally and this can result in asymmetric crimping and jamming of the second end 44 (i.e. proximal or outflow end) into the distal portion 1622. By locking one end 40 of the stent frame 32 to the distal portion 1622 with a locking configuration of the type illustrated in FIGS. 22-28 (e.g., utilizing a suture or the like 1760, 1850), the lock member and release member 1760, 1850 bears much of the cinching loads and prevents the distal end 40 of the stent frame 32 from moving proximally as the stent frame 32 is compressed. An added benefit is that when the stent frame 32 expands, the foreshortening of the stent frame 32 that occurs when the stent frame 32 expands is predictable. For example, if the inflow end 40 of the stent frame 32 is locked in longitudinal position, the stent frame 32 will always shorten towards or in the direction of the inflow end 40, which improves deployment predictability. The lock position of the stent frame 32 may be at multiple location along the stent frame 32 or just at inflow and outflow ends 40, 44, for example.

Figure 22:
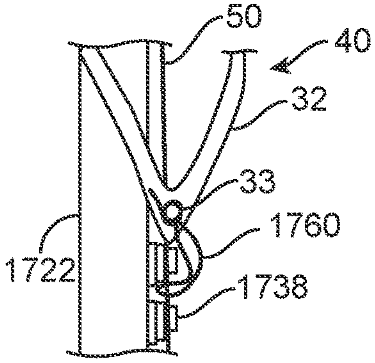
FIG. 22 is a partial, schematic illustration of one way in which one end of the stent frame can be locked in longitudinal and rotational position with respect to a distal portion of a delivery device.

Referring now also to FIG. 22, which illustrates one way in which the stent frame 32 can be secured over a distal portion 1722 and locked into position with a lock member 1760 being a flexible loop of material such as a suture or the like extending between an aperture 33 formed into the stent frame 32 and around the release member 50 that is positioned within a boss 1738 having an axis parallel to that of the distal portion 1722. If the suture 1760 is tight, rotational locking is present as well, which the user may need for torqueing the stented prosthesis into rotational alignment with a native valve, for example, to align a prosthetic valve and the native valve commissures to facilitate perfusion of the coronary arteries and to allow for future catheter access for coronary artery procedures. As can be seen, the aperture 33 is not a cell of the lattice of the stent frame 32 but the aperture 33 is formed within the material of the stent frame 32 (e.g., at a node, see also, FIG. 25) which defines the lattice. In the present embodiment, the release member 50 is an elongate pin ("release pin"). When in the configuration of FIG. 22, the stent frame 32 is locked in longitudinal position with respect to the distal portion 1722. When the release member 50 is proximally retracted to disengage from the lock member 1760, the stent frame 32 is unlocked and can move longitudinally and/or rotationally with respect to the distal portion 1722. In all other respects, the stent frame 32 and distal portion 1722 can be any of the types disclosed herein for use with delivery devices disclosed herein. The location of the suture 1760 can be positioned anywhere vertically along the stent frame 32, including providing multiple locks or sutures 1760 in multiple locations along the stent frame 32.

Figure 23:
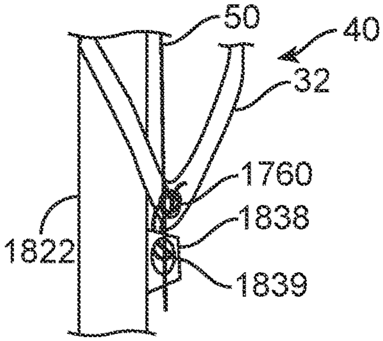
FIG. 23 is a partial, schematic illustration of another way in which one end of the stent frame can be locked in longitudinal and rotational position with respect to a distal portion of a delivery device.
Figure 24:
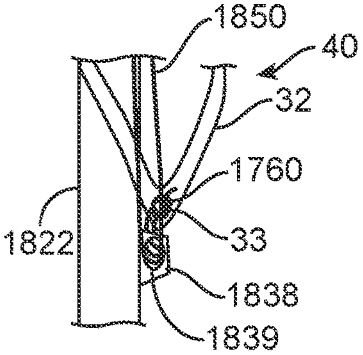
FIG. 24 is a partial, schematic illustration of yet another way in which one end of the stent frame can be locked in longitudinal and rotational position with respect to the distal portion of the delivery device of FIG. 23.

Similarly, FIG. 23 illustrates the stent frame 32 secured over a distal portion 1822 and having one end (distal end) 40 locked into position with the lock member 1760 extending between the aperture 33 formed in the stent frame 32 (as described with the prior embodiment) and around the release pin 50 that is positioned within a boss 1838 arranged orthogonal to the distal portion 1822. When in the configuration of FIG. 23, one end 40 of the stent frame 32 is locked in longitudinal position with respect to the distal portion 1822. When the release pin 50 is proximally retracted to disengage from the lock member 1760, the stent frame 32 is unlocked from the distal portion 1822 in that both ends of the stent frame 32 can move longitudinally and/or rotationally with respect to the distal portion 1822. The stent frame 32 and distal portion 1822 can be any of the type disclosed herein for use with delivery devices disclosed herein. FIG. 24 illustrates a substantially similar embodiment in which the release pin 50 is omitted and substituted with a release member being an elongate, flexible member (e.g., cord, suture or the like) 1850 that functions similarly to release pin 50 in that the release member 1850 is releasably engaged with the lock member 1760. Once the release member 1850 is released from lock member 1760, the lock member 1760 is released from the boss 1838 and the stent frame 32 can longitudinally and/or rotationally move with respect to the distal portion 1822 (i.e. transitions from being locked to unlocked). Rotational locking is also present in the locking features highlighted in FIGS. 22-24.

Figure 25:
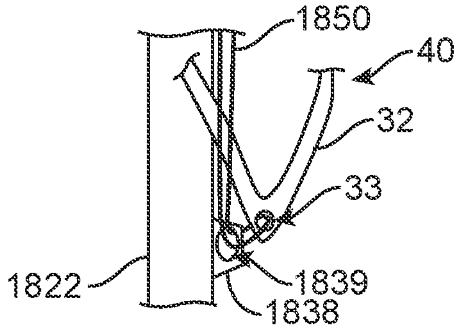
FIG. 25 is a partial, schematic illustration of another way in which one end of the stent frame can be locked in longitudinal position with respect to the distal portion of the delivery device of FIG. 23.
Figure 26:
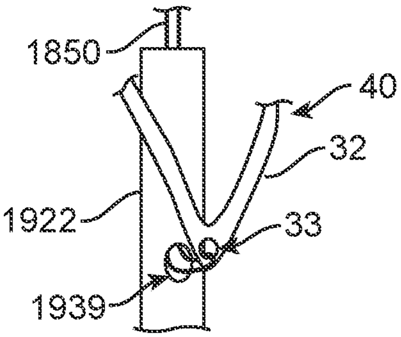
FIG. 26 is a partial, schematic illustration of an additional way in which one end of the stent frame can be locked in longitudinal and rotational position with respect to a distal portion of a delivery device.
Figure 27:
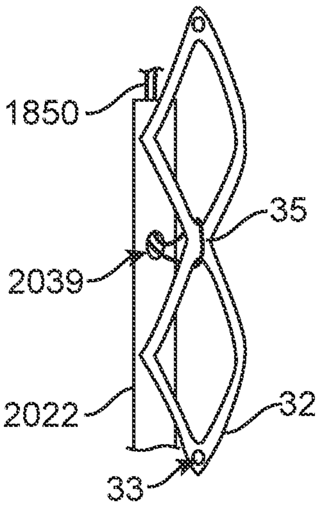
FIG. 27 is a partial, schematic illustration of a further way in which one end of the stent frame can be locked in longitudinal and rotational position with respect to a distal portion of a delivery device.

In another similar embodiment, as shown in FIG. 25, the lock member 1760 can be omitted. In this embodiment, the release member or suture 1850 can be routed both through aperture 1839 in the boss 1838 and the aperture 33 in the stented frame 32 to maintain the longitudinal and/or rotational position of the stent frame 32 with respect to the distal portion 1822. To unlock the stent frame 32, the release member 1850 can either be cut or the tension in the release member 1850 can otherwise be lessened to unlock the stent frame 32 from the distal portion 1822. Similarly, as shown in FIG. 26, the boss 1838 of FIG. 25 can be omitted and substituted with an aperture 1939 provided in a distal portion 1922. As shown in FIG. 27, the stent frame 32 can be longitudinally and/or rotationally locked in position (in both the compressed and expanded arrangements) with respect to the distal portion 2022 with the release member 1850 by providing an aperture 2039 in the distal portion 2022 and wrapping the release member 1850 around a node 35 of the stent frame 32. In these embodiments, the stent frame 32 is unlocked by releasing the release member 1850 from the stent frame 32 or otherwise sufficiently easing tension in the release member 1850 so that the stent frame 32 can move longitudinally with respect to the distal portion 1822, 1922, 2022. In all other respects, the stent frame 32 and distal portions 1822, 1922 and 2022 can be any of the types disclosed herein for use with delivery devices disclosed herein.

Figure 28:
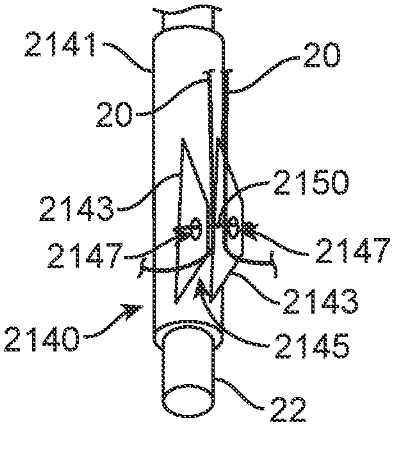
FIG. 28 is a partial, schematic illustration of a guide that can be secured to the distal portion.
Figure 29:
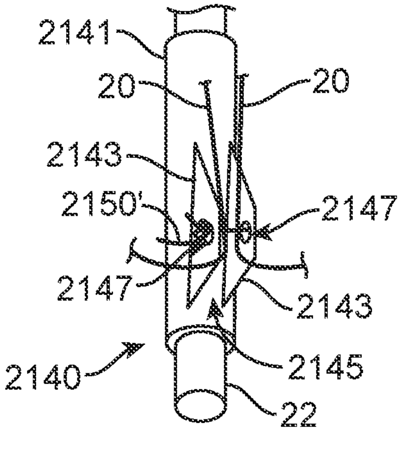
FIG. 29 is a partial, schematic illustration of an alternate guide that can be secured to the distal portion.

Turning now also to FIG. 28, which illustrates the distal portion 22 having at least one guide 2140. The guide 2140 includes a cylindrical body 2141 coaxially positioned over the distal portion 22. The guide 2140 also includes two trapezoidal-shaped projections 2143 extending from the body 2141 that collectively define a channel 2145 through which one or more tension members 20 can be routed, as shown. The projections 2143 also include an aperture 2147 through which a pin 2150 can be inserted. Collectively, slanted edges of the projection 2143 and the pin 2150 provide an atraumatic surface over which the tension members 20 can slide as they transition from a direction generally parallel to the distal portion 22 to a direction that is generally perpendicular to the distal portion 22 or vice versa, for example. In an alternate embodiment, as shown in FIG. 29, the pin 2150 of FIG. 28 can be replaced with a flexible member 2150', which can optionally be made of the same material as the tension member(s) 20 to reduce friction between the tension member(s) 20 and the flexible member 2150'.

Figure 30:
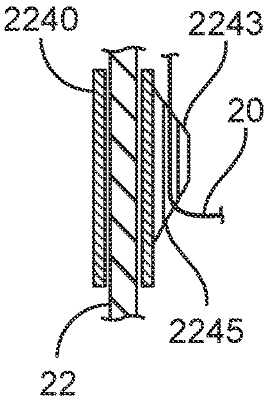
FIG. 30 is a partial, schematic illustration of another guide that can be secured to a distal portion.

Referring now also to FIG. 30, which illustrates an alternate guide 2240 positioned over the distal portion 22. The guide 2240 includes a boss 2243 defining a channel 2245 in which one or more tension members 20 can be routed, as shown. Similar to the projections 2143 of FIGS. 29-30, the boss 2243 has a generally trapezoidal cross-section and is configured to provide an atraumatic surface over which the tension members 20 can slide as they transition from a direction generally parallel to the distal portion 22 to a direction that is generally perpendicular to the distal portion 22 or vice versa. It will be understood that multiple guides 2240 can be provided on the distal portion 22.

Figure 31:
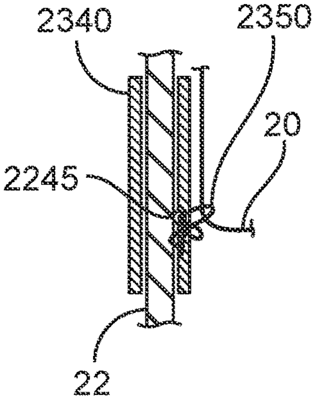
FIG. 31 is a partial, schematic illustration of yet another guide that can be secured to the distal portion.

Turning now also to FIG. 31, which illustrates an alternate guide 2340 having an aperture 2345 through which a flexible member is threaded to form a loop 2350. One or more of the tension members 20 can be routed through the loop 2350, which are positioned to provide an atraumatic surface over which the tension members 20 can slide as they transition from a direction generally parallel to the distal portion 22 to a direction that is generally perpendicular to the distal portion 22 or vice versa, for example. It will be understood that multiple guides 234 can be provided along a length of the distal portion 22.

Figure 32:
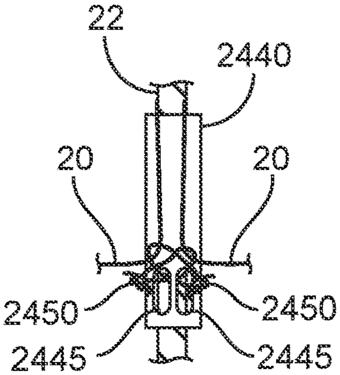
FIG. 32 is a partial, schematic illustration of an alternate guide that can be secured to the distal portion.

Referring now also to FIG. 32 which illustrates an alternate guide 2440 having two apertures 2445 through which respective flexible members are threaded to form loops 2450. One or more of the tension members 20 can be routed through each of the loops 2450. The loops 2450 respectively provide an atraumatic surface over which the tension members 20 can slide as they transition from a direction generally parallel to the distal portion 22 to a direction that is generally perpendicular to the distal portion 22 or vice versa, for example. In some embodiments, the loops 2450 are made of the same material as the tension members 20 to further reduce friction. It will be understood that multiple guides 2440 can be provided on the distal portion 22.

Figure 33:
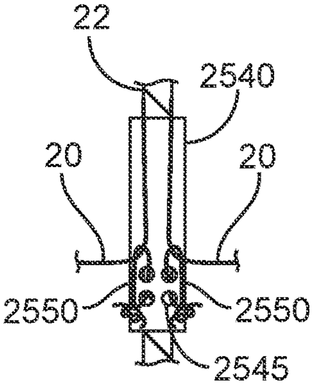
FIG. 33 is a partial, schematic illustration of another guide that can be secured to the distal portion.

Similarly, FIG. 33 illustrates an alternate guide 2540 having four apertures 2545 (generally referenced) through which respective flexible members are threaded to form loops 2550. One or more of the tension members 20 can be routed through each of the loops 2550. The loops 2450 respectively provide an atraumatic surface over which the tension members 20 can slide as they transition from a direction generally parallel to the distal portion 22 to a direction that is generally perpendicular to the distal portion 22 or vice versa. In some embodiments, the loops 2550 are made of the same material as the tension members 20.

Figure 34A:
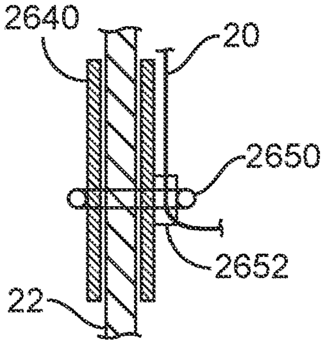
FIG. 34A a partial, cross-sectional schematic illustration of yet another guide having a ring that can be secured to the distal portion.
Figure 34B:
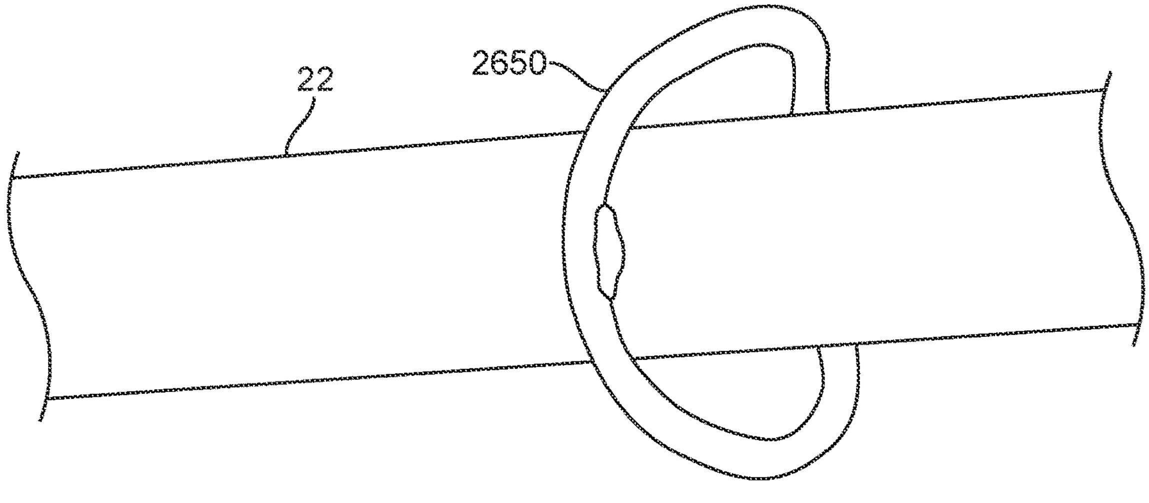
FIG. 34B is a side view of the ring of FIG. 34A being directly secured to the distal portion.

Turning now also to FIG. 34A which illustrates an alternate guide 2640 having a ring 2650 through which one or more tension members 20 are threaded. The ring 2650 provides an atraumatic surface over which the tension members 20 can slide as they transition from a direction generally parallel to the distal portion 22 to a direction that is generally perpendicular to the distal portion 22 or vice versa, for example. Optionally, the guide 2640 can also include a support or divider 2652. In other alternate embodiments, as shown in FIG. 34B, the ring 2650 can be directly welded or otherwise attached to the distal portion 22. It will be understood that multiple guides 2640 can be provided on the distal portion 22.

Figure 35:
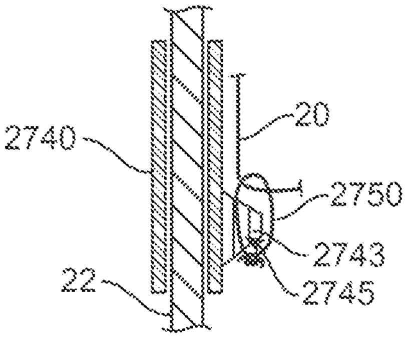
FIG. 35 is a partial, schematic illustration of an alternate guide that can be secured to the distal portion.

Referring now also to FIG. 35, which illustrates yet another alternate guide 2740 positioned over the distal portion 22. The guide 2740 includes a boss 2743 defining a channel 2745 in which a loop 2750 can be secured. Through the loop 2750, one or more tension members 20 can be routed. The loop 2750 is configured to provide a rounded, atraumatic surface over which the tension members 20 can slide as they transition from a direction generally parallel to the distal portion 22 to a direction that is generally perpendicular to the distal portion 22 or vice versa. In some embodiments, the loop 2750 is made of the same material as the tension members 20 as discussed with respect to prior embodiments. It will be understood that multiple guides 2740 can be provided on the distal portion 22.

Figure 36:
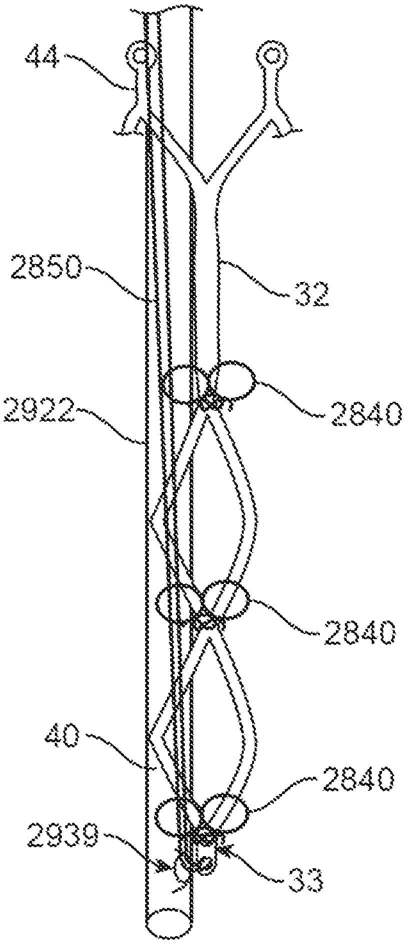
FIG. 36 is a partial, schematic illustration of the stent frame having guide loops secured thereto and one end of the stent frame being longitudinally locked with respect to a distal portion.

In further embodiments, as generally shown in FIG. 36, the guides discussed above can be replaced with transition elements 2840 that are flexible loops secured to the stent frame 32. In this embodiment, three sets of flexible loops 2840 are provided on the stent frame 32 for tension members (not shown, see prior disclosed embodiments) to be routed through and to reduce wear on the tension members as they change direction with respect to the distal portion 22. In this embodiment, the stent frame 32 is longitudinally and/or rotationally locked in position (in both the compressed and expanded arrangements) with any of the locking configurations of FIGS. 22-27. In the illustrated embodiment, the distal portion is configured similarly to that shown in FIG. 26. In this way, a distal portion 2922 is provided with an aperture 2939 through which a suture 2850 of the like is threaded to selectively release the stent frame 32 from the distal portion 2922.

Figure 37:
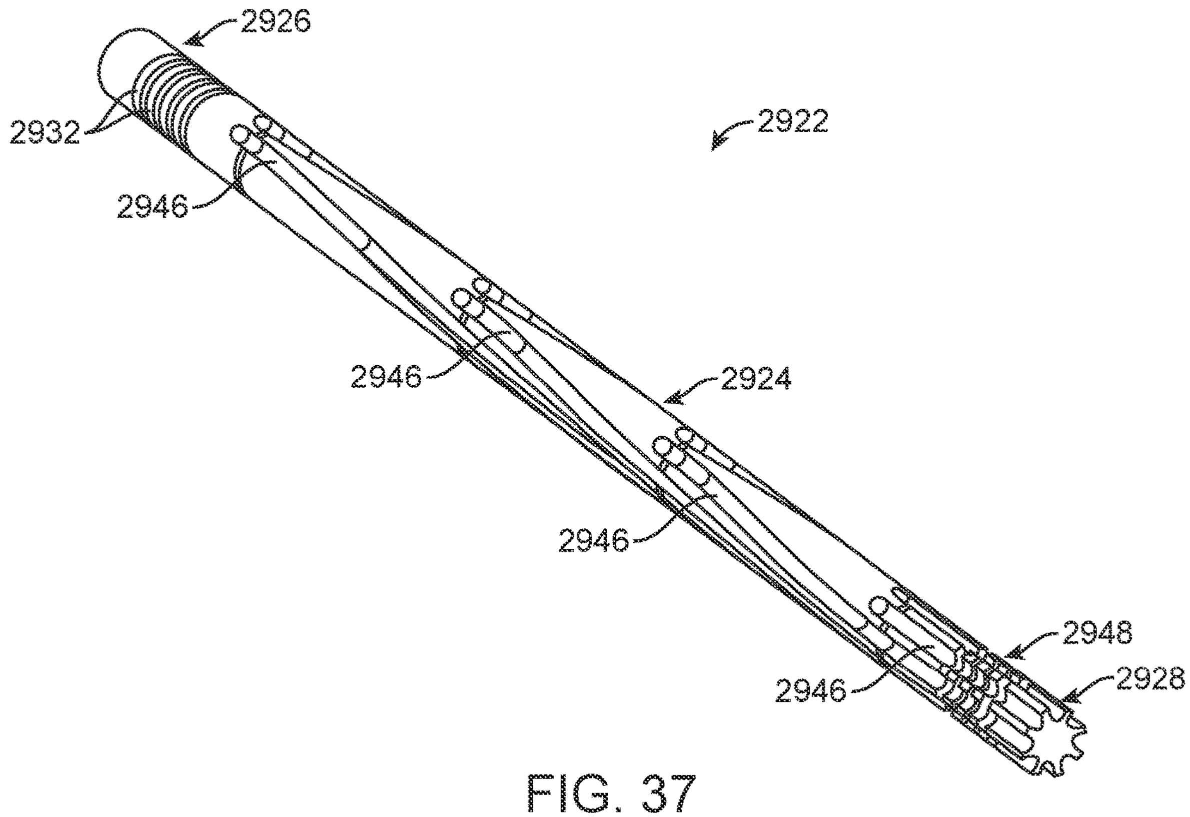
FIG. 37 is a partial, perspective view of an alternate distal portion having generally spiral cut channels similar to the embodiment of FIG. 7E.
Figure 38:
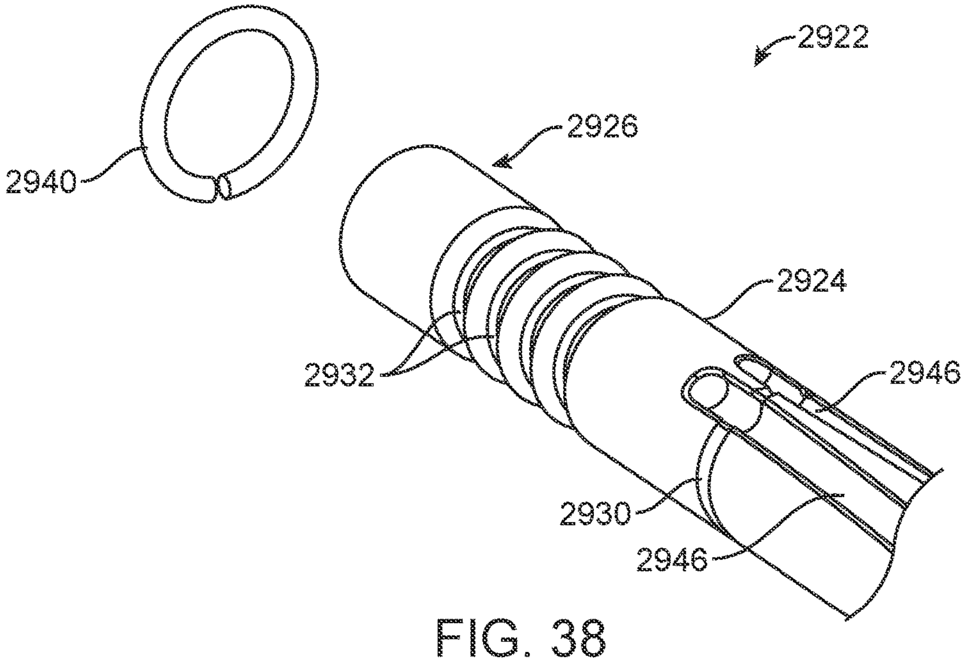
FIG. 38 is a partial, exploded view of a transition element and the distal portion of FIG. 37.
Figure 39:
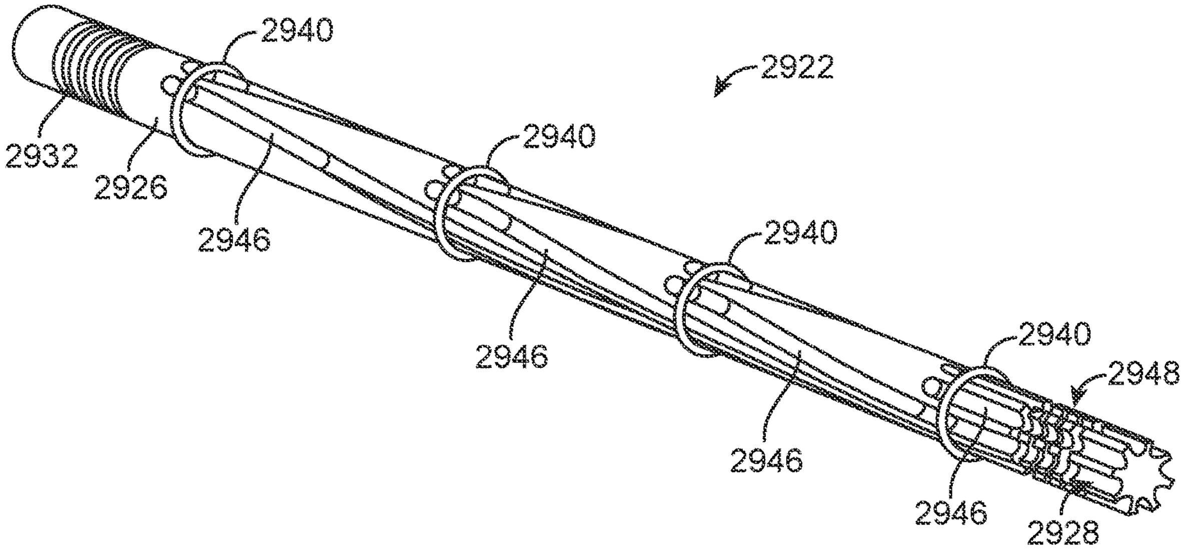
FIG. 39 is a perspective view of the assembled distal portion of FIGS. 37-38.

Turning now also to FIGS. 37-39, which collectively illustrate an alternate distal portion 2922 having a body 2924 with first and second ends 2926, 2928. The distal portion 2922 can be used as a substitute for the distal portion 22 of FIG. 1, for example. Similar to what is shown in FIG. 7E, the body 2924 includes a plurality of generally spiral channels 2946 and a plurality of notches 2930 for receiving transition elements 2940, which can be split rings or the like. The transition elements 2940 function similar to the cage members 344 of FIGS. 7A-7D and provide for a rounded, atraumatic surface for one or more tension members (not shown) to travel over from the prosthetic heart valve (not shown) to the channels 2946. The transition elements 2940 can be optionally be welded to the body 2924. In alternate embodiments, the transition elements 2940 are positioned and oriented in different way (e.g., similar to the embodiments shown in FIG. 8A or 9, for example). In such alternate embodiments, the transition elements 2940 can be welded or electrojoined to the body 2924, as desired.

As best shown in FIG. 38, the first end 2926 further includes a flexible section 2932 collectively defined by a plurality of notches. The flexible section 2932 has an increased flexibility with respect to other portions of the body 2924 that can be beneficial as the distal portion 2922 navigates an aortic arch. Similarly, the second end 2928 also includes a flexible section 2948 defined by a plurality of features similar to bellows. It is envisioned that any number of flexible sections can be provided and that one or more flexible sections can be provided elsewhere on the device. The distal portion 2922 can be used as a substitute for the distal portion of FIG. 1, for example, or can be used with an alternate delivery device.

Figure 40:
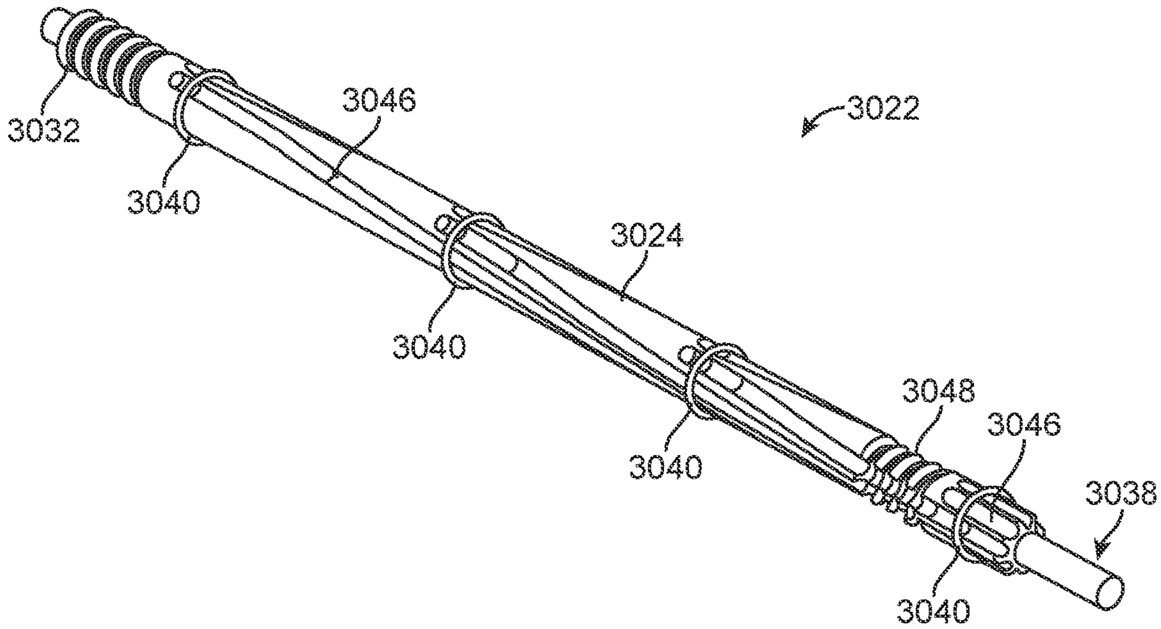
FIG. 40 is a perspective view of an alternate distal portion.
Figure 41:
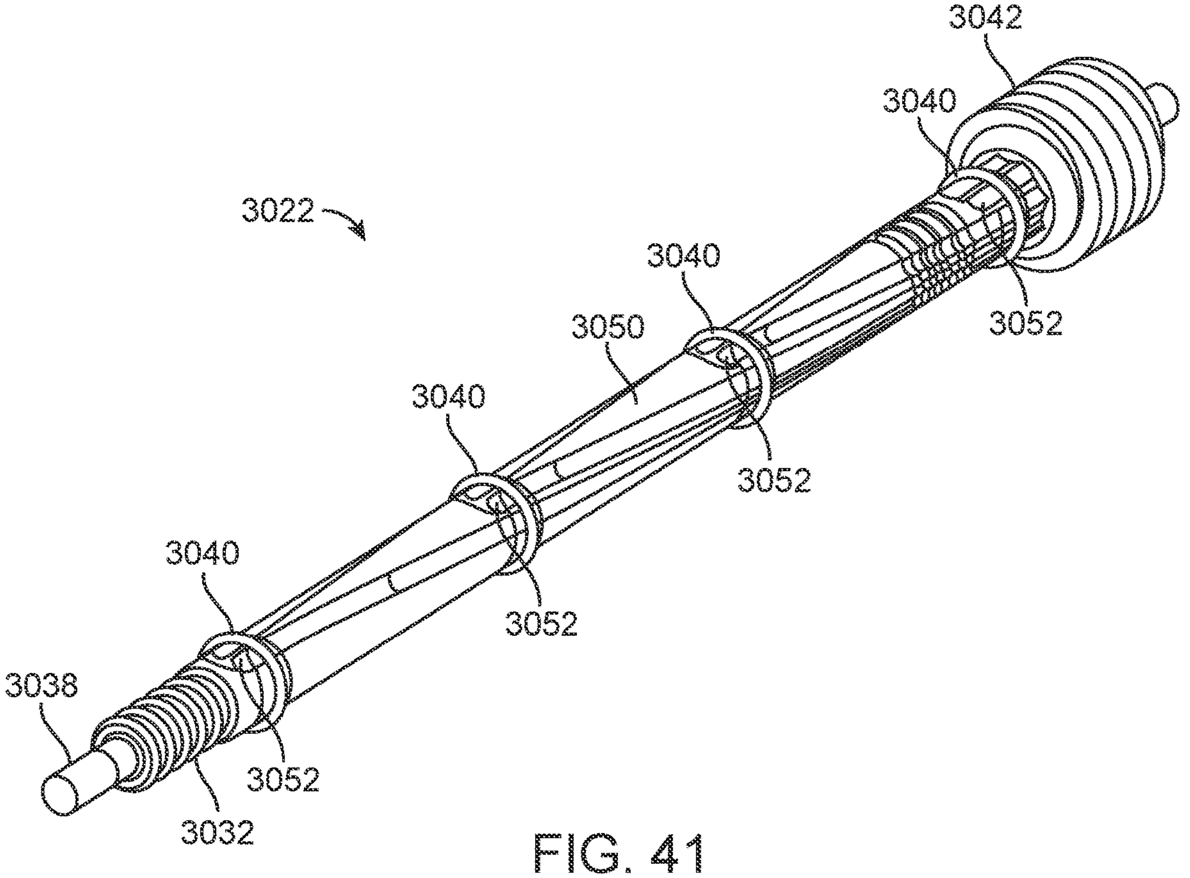
FIG. 41 is a perspective view of the distal portion of FIG. 40 further including a wrap and a hub.
Figure 42:
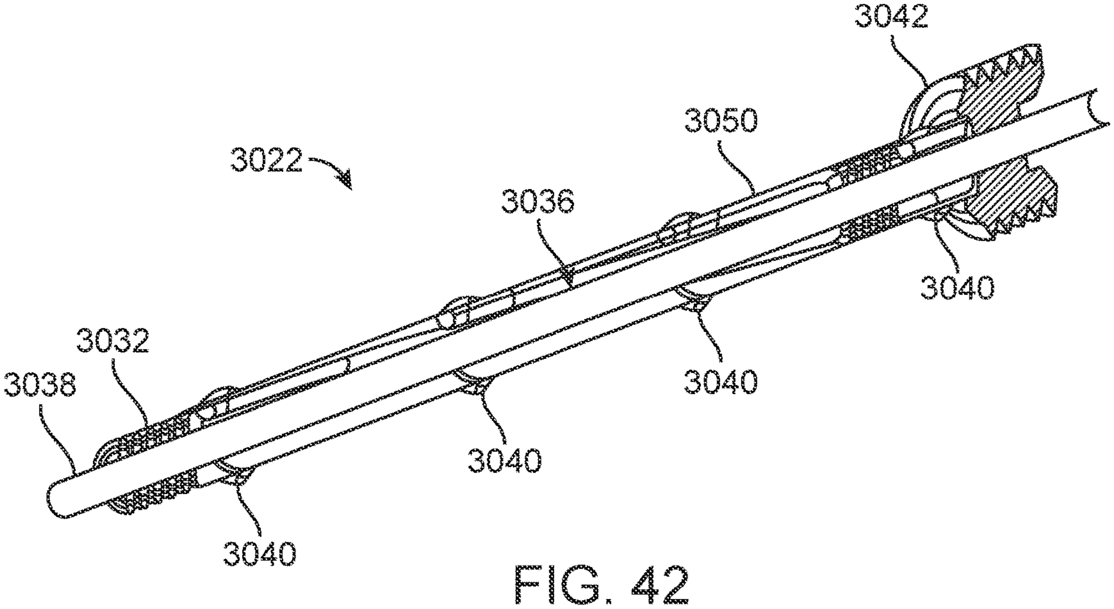
FIG. 42 is a cross-sectional view of the distal portion of FIG. 41.

Turning now also to FIGS. 40-42, which illustrate an alternate distal portion 3022 that includes a body 3024 having two flexible sections 3032, 3048 similar to the flexible sections 2932, 2948 described above. The body 3024 further defines a lumen 3036 through which an extension member 3038 can be positioned for attachment to a hub 3042 at a second end 3028 of the body 3024. In some embodiments, the extension member 3038 is hollow so that a guide wire (e.g., the guide wire 28 of FIG. 1) can be inserted therethrough. The distal portion 3022 can be used as a substitute for the distal portion of FIG. 1, for example, or can be used with an alternate delivery device.

The distal portion 3022 can further optionally include a heat shrink wrap 3050 as generally referenced in FIG. 42. The heat shrink wrap 3050 is arranged and configured to generally enclose the channels 3046 and includes openings 3052 for one or more tension members (not shown). One advantage of enclosed channels 3046 is improved tension member loading as the tension members cannot cross or interact with one another. The openings 3052 can be formed via cutting or otherwise and are located proximate the tension member transition areas (i.e. where the start of each channel 3046 meets one respective transition element 3040). The heat shrink wrap 3050 can be made of any biocompatible material including Teflon® (PTFE) and polyester, for example.

Figure 43:
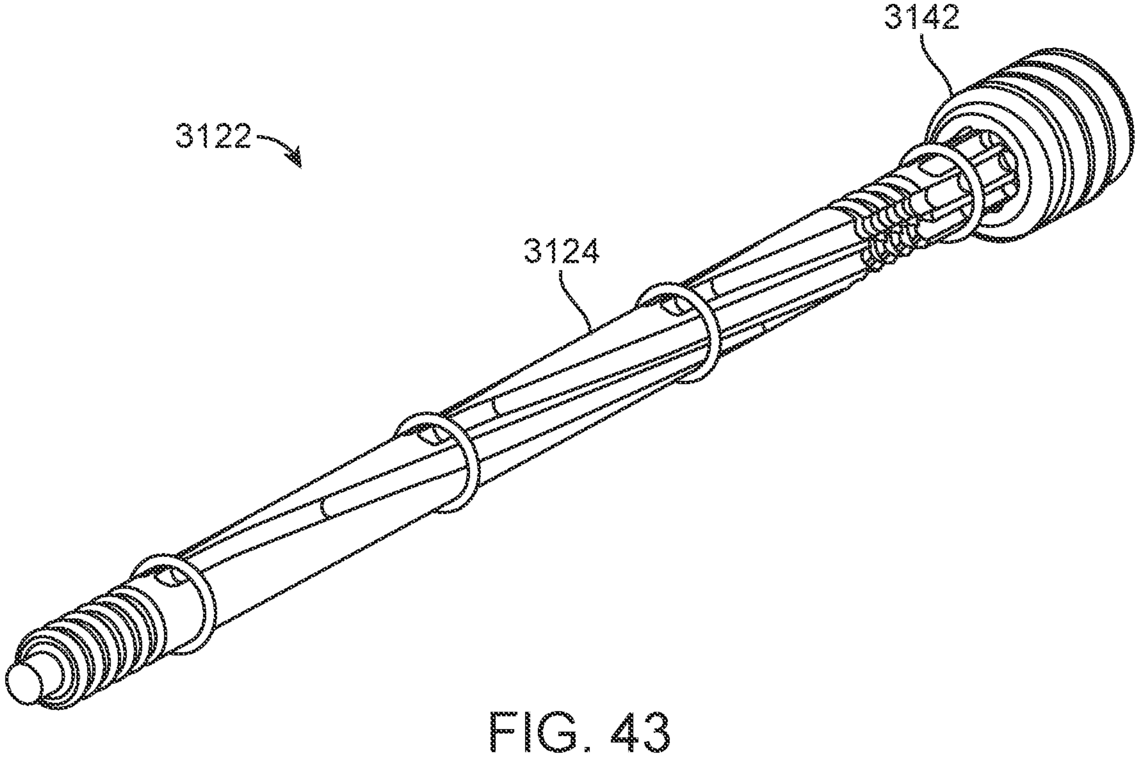
FIG. 43 is a perspective view of an alternate distal portion substantially similar to those of FIGS. 37-42 having an integrated hub.
Figure 44:
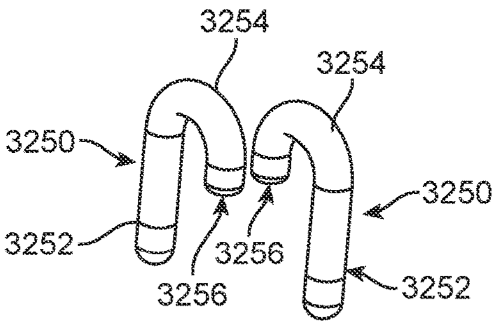
FIGS. 44-47 illustrate select components of an alternate distal portion having a plurality of transition elements through which tension members can be routed.
Figure 45:
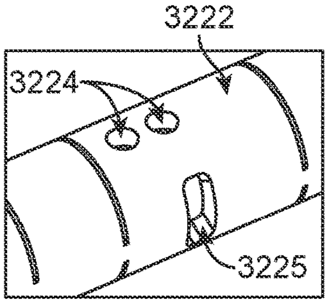
Figure 46:
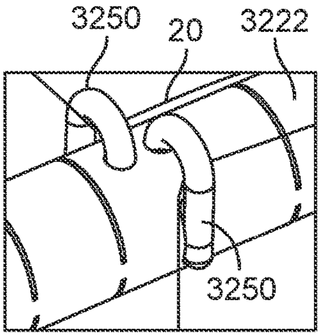
Figure 47:
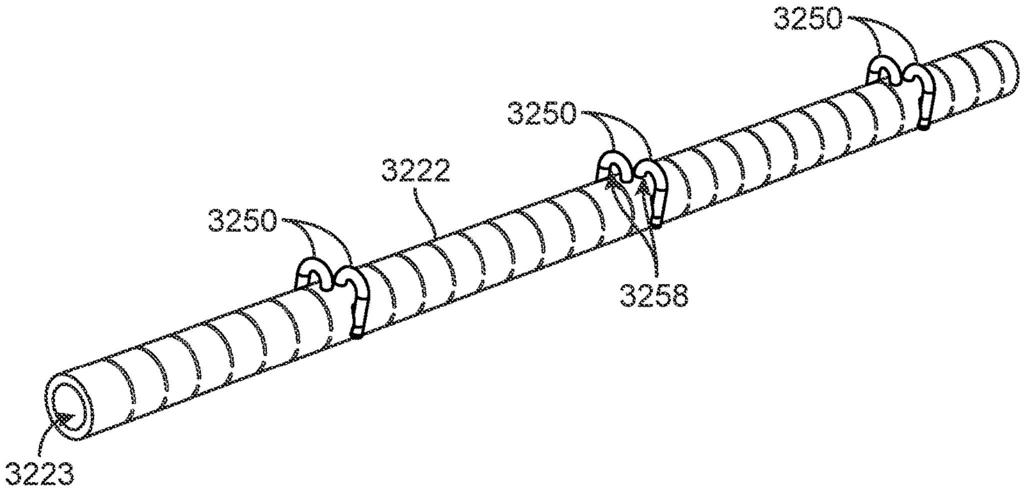
Figure 48:
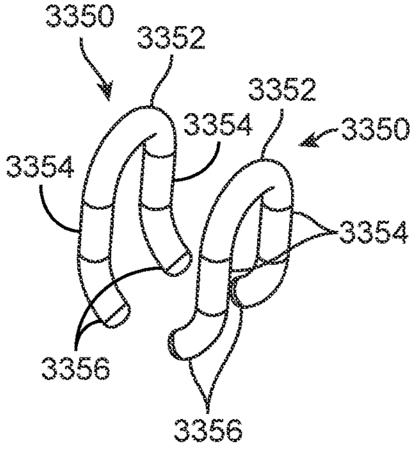
FIGS. 48-51 illustrate select components of an alternate distal portion having a plurality of transition elements through which tension members can be routed.
Figure 49:
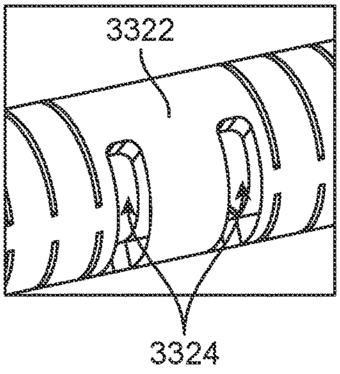
Figure 50:
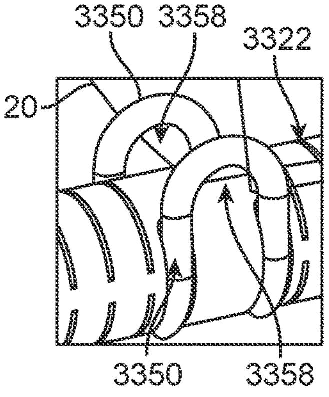
Figure 51:
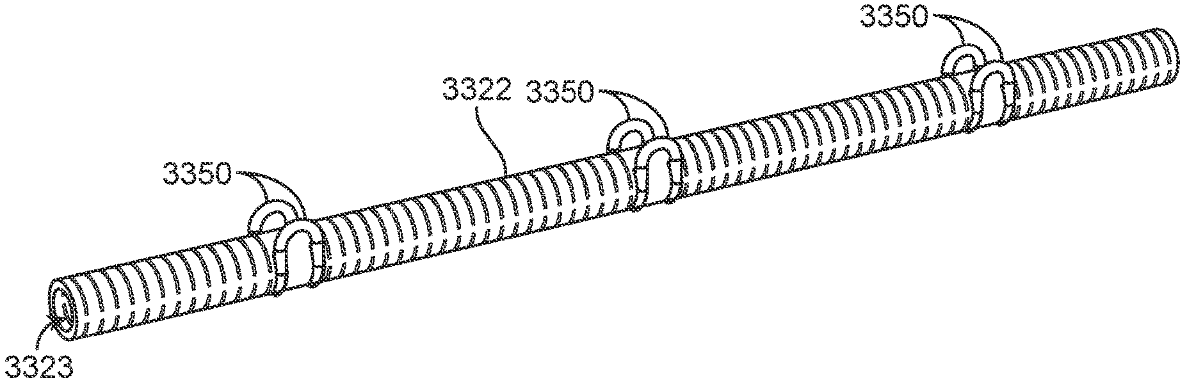

Referring now also to FIG. 43, which illustrates a distal portion 3122 that can be substituted for the distal portion 22 of FIG. 1, for example. The distal portion 3122 is electroformed and can optionally include a body 3124 with an integrated hub 3142. As illustrated, the hub 3142 can be threaded or can alternatively be snapped on to the body 3124. The distal portion 3122 can otherwise be arranged, configured and function similar to the embodiments of FIGS. 37-42 or other embodiments disclosed herein. The distal portion 3122 can be used as a substitute for the distal portion of FIG. 1, for example, or can be used with an alternate delivery device.

Referring in addition now to FIGS. 44-47 which illustrate select components of an alternate distal portion 3222 that can be substituted for the distal portion 22 of FIG. 1, for example. A plurality of transition elements 3250 are spaced along a length of the distal portion 3222 for receiving one or more tension members 20 of the type disclosed herein for compressively retaining a stented prosthesis (not shown) to the distal portion 3222 in a manner described above with respect to other embodiments. Only one tension member 20 is partially shown in FIG. 46 for ease of illustration, see also FIG. 56, which is similar in concept. In one illustrative embodiment, the distal portion 3222 can include six transition elements 3250 mounted into and positioned exterior with respect to a central lumen 3223 of the distal portion 3222. Each transition element 3250 is generally cane shaped having a straight portion 3252 connected to a curved portion 3254 having an end 3256. The curved portion 3254 and the distal portion 3222 collectively define a lumen 3258 (only a select few of which are referenced for ease of illustration in FIG. 47) through which the one or more tension members 20 can be routed. At one of the transition elements 3250, each tension member 20 will change direction and wrap around the transition element 3250 as discussed above with respect to other embodiments (i.e. the transition elements 3250 are positioned proximate a location where at least one tension member 20 transitions from a first orientation that is not parallel to the distal portion 3222 to a second orientation that is generally parallel to the distal portion 3222 or vice versa). For example, each tension member 20 will be routed in a distal direction parallel along the length of the distal portion 3222, through at least one transition element 3250 and then turn to wrap around the stented prosthesis, which is loaded onto the distal portion 3222. Once the transition element wraps around the stented prosthesis, the tension member 20 is routed through the adjacent transition element 3250 and back proximally along the length of the distal portion 3222 to the handle assembly or the like. In one embodiment, the distal portion 3222 includes apertures 3224, 3225 (FIG. 45) for receiving and mounting each transition element 3250 via welding or the like to keep the profile of the distal portion 3222 as small as possible (FIG. 46), which can reduce vascular complications. The ends 3256 can be inserted into apertures 3224 and the straight portions 3252 can be inserted within apertures 3225 on opposing sides of the distal portion 3222 (only one side aperture 3225 is shown, however, the second aperture an opposing side of the distal portion 3222 is identical to that shown in FIG. 45). As with prior disclosed embodiments, the transition elements 3250 define a smooth rounded outer surface over which the tension members 20 can change direction, which reduces wear on the tension members 20. In all other respects, the distal portion 3222 can be any of the type disclosed herein for use with delivery devices disclosed herein.

Referring in addition now to FIGS. 48-51, which illustrate select components of an alternate distal portion 3322 that can be substituted for the distal portion 22 of FIG. 1, for example. A plurality of transition elements 3350 are spaced along a length of the distal portion 3322 for receiving one or more tension members 20 of the type disclosed herein for compressively retaining a stented prosthesis (not shown) to the distal portion 3322. Only one tension member 20 is partially shown in FIG. 50 for ease of illustration, see also FIG. 56, which is similar in concept. In one illustrative embodiment, the distal portion 3322 can include six transition elements 3350 mounted generally parallel to one another. The transition elements 3350 are each positioned exterior with respect to a central lumen 3323 of the distal portion 3322. Each transition element 3350 includes two straight portions 3354 interconnected by a curved portion 3352. Opposite the curved portion 3352, each straight portion 3354 can include a foot 3356 that mirrors the contour of the distal portion 3322. The curved portion 3352 and the distal portion 3322 collectively define a lumen 3358 (FIG. 50) through which the one or more transition elements 3350 can be routed. At one of the transition elements 3350, each tension member 20 will change direction and wrap around the transition element 3350, proximate the curved portion 3352, similar to other disclosed embodiments (i.e. the transition elements 3350 are positioned proximate a location where at least one tension member 20 transitions from a first orientation that is not parallel to the distal portion 3322 to a second orientation that is generally parallel to the distal portion 3322 or vice versa). For example, each tension member 20 will be routed in a distal direction parallel along the length of the distal portion 3322, then turn through one lumen 3358 to wrap around the stented prosthesis, which is loaded onto the distal portion 3322. Once the tension member 20 wraps around the stented prosthesis, the tension member 20 is routed through the lumen 3358 of the adjacent transition element 3350 on the opposite side of the distal portion 3322 and back proximally along the distal portion 3322 to the handle assembly or the like. In one embodiment, the distal portion 3322 includes apertures 3324 (FIG. 49) for receiving and mounting each transition element 3350 via welding or the like to keep the profile of the distal portion 3350 as small as possible (FIG. 50), which can reduce vascular complications. As with prior disclosed embodiments, the transition elements 3350 define a smooth rounded outer surface over which the tension members 20 can change direction, which reduces wear on the tension members 20. In all other respects, the distal portion 3322 can be any of the type disclosed herein for use with delivery devices disclosed herein.

Figure 52:
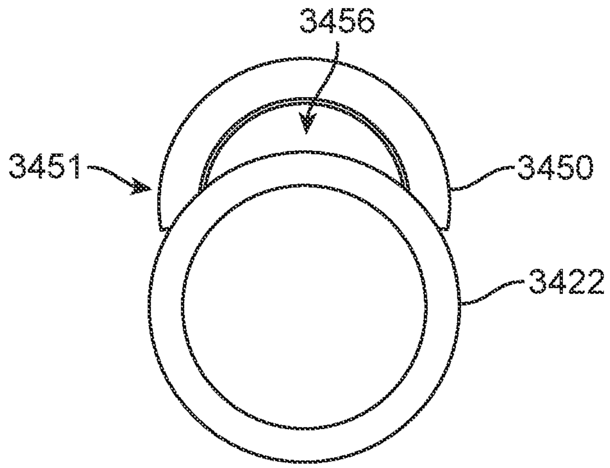
FIGS. 52-54 illustrate select components an alternate distal portion having a plurality of transition elements through which tension members can be routed.
Figure 53:
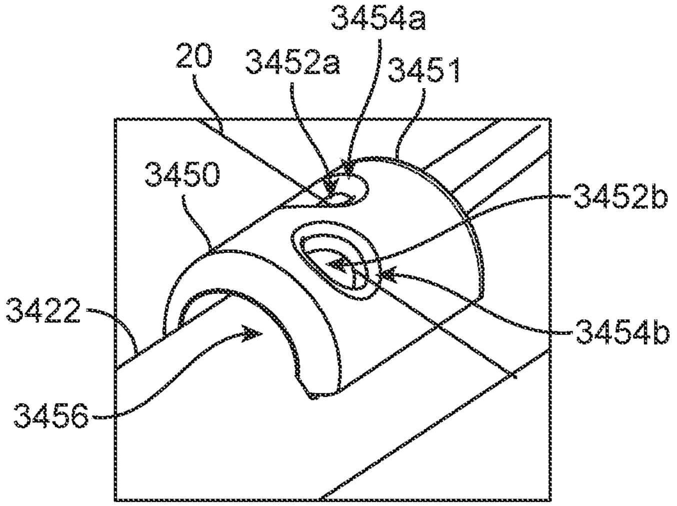
Figure 54:
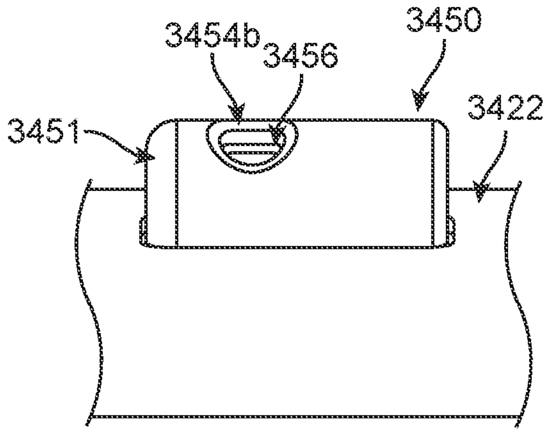

For embodiments disclosed herein, a rounded, smooth surface of a transition element can be formed using a laser welder to break the edge of a hole or aperture through or over which the tension member is routed in the transition element. One example that can utilize this technique, among other disclosed herein, is shown in FIGS. 52-54. In this embodiment, only a short length of a distal portion 3422 is illustrated, however, it will be understood that the distal portion 3422 can be similar to those disclosed above, except as explicitly stated. Attached to an outer surface of the distal portion 3422 are one or more transition elements 3450 (only one is shown). Each transition element 3450 includes a semi-circular body 3451 in which two apertures 3452*a*, 3452*b* are formed. The apertures 3452*a*, 3452*b* can optionally be offset along a length of the body 3451, as illustrated. Each aperture 3452*a*, 3254*b* includes a smooth, rounded surface 3454*a*, 3254*b* over which one or more tension members 20 can be routed and over which the tension members 20 can change direction (i.e. the transition elements 3450 are positioned proximate a location where at least one tension member 20 transitions from a first orientation that is not parallel to the distal portion 3422 to a second orientation that is generally parallel to the distal portion 3422 or vice versa). The transition element 3450 and distal portion 3422 collectively form a lumen 3456 in which one or more tension members 20 can be routed. In one illustrative embodiment, one tension member 20 is routed parallel along the length of the distal portion 3422 in a distal direction, into the lumen 3456, out of the first aperture 3452*a*, changes direction and then around the stented prosthesis (not shown) in ways disclosed above with respect to other embodiments. Once the tension member 20 wraps substantially all the way around the stented prosthesis, the tension member 20 is routed through the second aperture 3254*b*, into the lumen 3456 and then proximally back to the handle assembly (not shown). Multiple tension members 20 (e.g., proximal, waist and distal tension members) can be routed in a similar fashion. When multiple tension members 20 are provided, multiple tension members 20 may be routed through lumens 3456 as they are directed to the appropriate locations along the length of the distal portion 3422. The distal portion 3422 can be used as a substitute for the distal portion of FIG. 1, for example, or can be used with an alternate delivery device.

Figure 55:
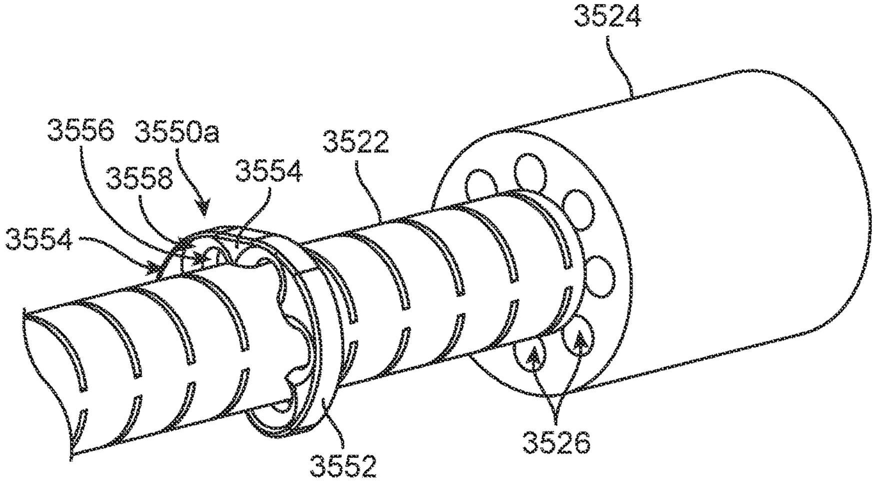
FIGS. 55-56 illustrate select components an alternate distal portion having a plurality of transition elements through which tension members can be routed.
Figure 56:
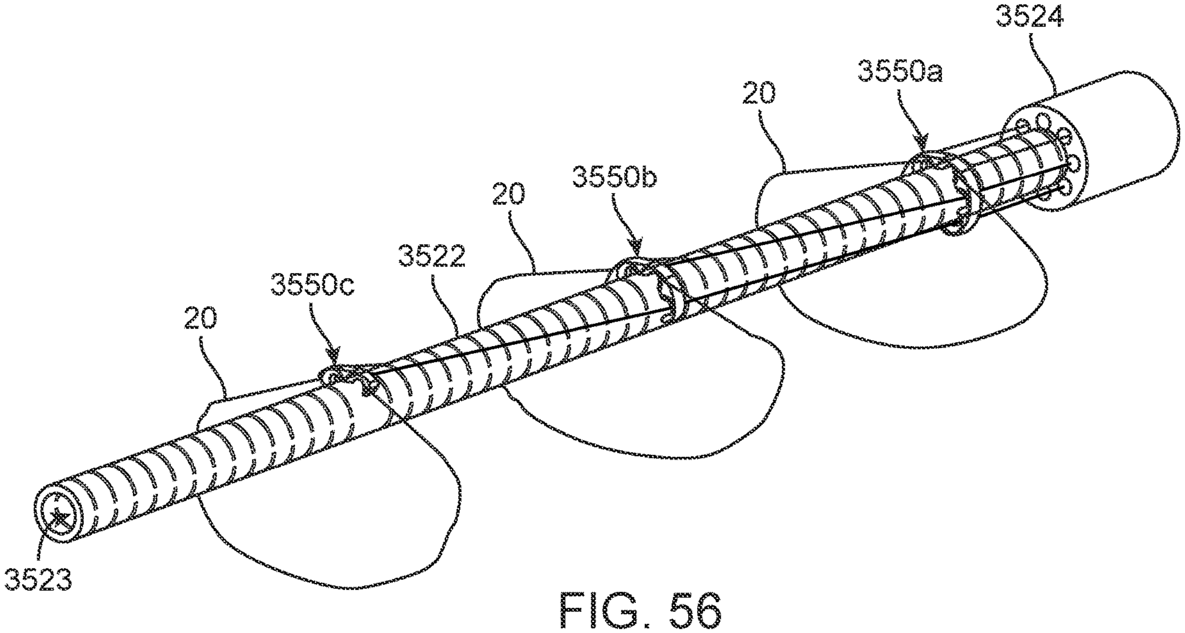

Referring in addition now to FIGS. 55-56, which illustrate select components of an alternate distal portion 3522 that can be substituted for the distal portion 22 of FIG. 1, for example. A plurality of transition elements 3550*a*, 3550*b*, 3550*c* are spaced along a length of the distal portion 3522 for receiving one or more tension members 20 (FIG. 56) of the type disclosed herein for compressively retaining a stented prosthesis (not shown) to the distal portion 3522. It is noted that FIG. 56 conceptually illustrates one tension member routing configuration suitable for all embodiments disclosed herein for use with various optional transition elements, distal portions and delivery devices disclosed herein. For organization of a plurality of tension members 20, a hub 3524 can be provided having a plurality of circumferentially spaced apertures 3526 (only a select few of which are referenced in FIG. 55 for ease of illustration). In one illustrative embodiment, the distal portion 3522 can include three transition elements 3550*a*, 3550*b*, 3550*c* mounted along the length of the distal portion 3522. The transition elements 3550*a*, 3550*b*, 3550*c* are each positioned exterior with respect to a central lumen 3523 of the distal portion 3522. Each transition element 3550*a*, 3550*b*, 3550*c* includes a rounded outer body 3552 from which a plurality of arms 3554 (only two of which is referenced in FIG. 55 for ease of illustration) extend radially in the direction of the distal portion 3522. Each arm 3554 is configured to contact the distal portion 3522 so that a plurality of lumens 3556 are formed between two adjacent arms 3554, the outer body 3552 and the distal portion 3522. Within each lumen 3556, one or more tension members 20 can be routed. After extending through one of the lumens 3556, each tension member 20 will change direction and wrap around the respective transition element 3550_a_, 3550_b_, 3550_c_ as discussed above with respect to other embodiments. Therefore, each lumen 3556 defines a smooth, rounded surface 3558 to prevent wear on the tension member 20 as it changes direction (i.e. the transition elements 3550_a_, 3550_b_, 3550_c_ are positioned proximate a location where at least one tension member 20 transitions from a first orientation that is not parallel to the distal portion 3522 to a second orientation that is generally parallel to the distal portion 3522 or vice versa). In one example embodiment, as generally illustrated in FIG. 56, each tension member 20 will be routed from its own aperture 3526 in the hub 3524 parallel along the length of the distal portion 3522, then turn after exiting one lumen 3556 of one transition element 3550_a_, 3550_b_, 3550_c_ to wrap around the stented prosthesis as described with respect to other embodiments. Once the tension member 20 wraps around the stented prosthesis, the tension member 20 is routed through another lumen 3556 of the same transition element 3550_a_, 3550_b_, 3550_c_ and back proximally along the distal portion 3522 to the hub 3524 and the handle assembly or the like. In one embodiment, the hub 3524 is configured to have a sufficient number of apertures 3526 so that each aperture 3526 houses, at a maximum, one length of one respective tension member 20 (e.g., if three tension members 20 are provided, the hub 3524 includes at least six apertures 3526). This configuration limits the opportunity for the tension members 20 to tangle and snag. As it can be seen in FIG. 56, the number of arms 3554, and thus the number of lumens 3556, for each transition element 3550_a_, 3550_b_, 3550_c_ can vary as desired. In one illustrative example, the distal transition element 3550_c_ includes three arms defining two lumens, the waist transition element 3550_b_ includes four arms defining three lumens and the proximal transition element 3550_a_ includes five arms defining four lumens. Although the lumens and apertures of the waist and distal transition elements 3350_b_, 3550_c_ are not labeled, they are identically configured to those shown and described with respect to the proximal transition element 3550_a_, except in number. The number of arms 3554 and lumens 3556 for all transition elements 3550_a_, 3550_b_, 3550_c_, as well as the number of transition elements provided can vary, as desired. Alternatively, if multiple transition elements are provided, they can be identically configured. In all other respects, the distal portion 3522 can be any of the type disclosed herein for use with delivery devices disclosed herein.

For all embodiments disclosed herein, the transition element(s) can be considered part of the distal portion or can be considered a separate element. For all embodiments disclosed herein, the transition elements can be made of a material having a very fine surface finish, (e.g., less than 20 micro inch root mean square (RMS); in some embodiments less than 6 RMS). In all embodiments herein, transition elements and other smooth surfaces can be formed by laser ablation, extrude honing and tumbling, for example.

For many of the embodiments disclosed above, the tension members are routed along an outer surface of the distal portion. Such embodiments are believed to be beneficial because when the tension members change direction, less of a moment arm is applied to the respective transition elements, which reduces the tendency for the distal portion to buckle.

In view of the present disclosure, embodiments include a delivery device for delivering a stented prosthesis to a target site. The delivery device comprises an elongate tension member that can compressively retains the stented prosthesis to the delivery device and a shaft assembly having a distal portion configured to retain the stented prosthesis. The shaft assembly further including a transition element secured to the distal portion, the transition element at least partially defining a lumen; wherein the elongate tension member extends in a first direction distally along a length of the distal portion. The elongate tension member is then routed through the lumen and then extends in a second direction that is different than the first direction. The transition element provides a rounded edge over which the tension member contacts as the tension member extends from the first direction to the second direction. In some embodiments, a plurality of elongate tension members are provided and a plurality of transition elements spaced along a length of the distal portion. Some embodiments include the stented prosthesis, wherein the second direction is around the stented prosthesis. In some embodiments, the transition element has a surface finish less than 20 micro inch RMS. In some embodiments, the transition element includes a straight portion connected to a curved portion; wherein the curved portion at least partially defines the lumen. In some embodiments, the curved portion includes an end that is secured to the distal portion. In some embodiments, the delivery device includes six transition elements provided in pairs, each pair being two of the six transition elements. In some embodiments, the two transition elements of each pair are offset with respect to one another. In some embodiments, the two transition elements of each pair are parallel with respect to one another. In some embodiments, the transition element includes an outer body having a plurality of arms extending radially toward the distal portion. In some embodiments, the distal portion includes a hub having a plurality of apertures through which the tension member is routed. In some embodiments, the apertures are circumferentially spaced. In some embodiments, the tension member extends through two apertures of the hub. In some embodiments, the lumen is defined by the transition element and the distal portion. In some embodiments, the transition element extends around less than an entirety of a circumference of the distal portion. In some embodiments, the distal portion defines a plurality of apertures for receiving the transition element. Some embodiments include a plurality of transition elements that are identically shaped. In some embodiments, the lumen defines a plane that is perpendicular to the distal portion. In some embodiments, the transition element extends radially from the distal portion.

In view of present disclosure, embodiments include a combination of a stented prosthesis loaded to a delivery device. The combination comprises a stented prosthesis including a stent frame having a compressed arrangement and an expanded arrangement; wherein the stent frame includes a distal end and a proximal end and an aperture provided at one or more ends, e.g., at the distal end. The combination further includes a delivery device having a distal portion on which the stented prosthesis is loaded. The delivery device includes a release member extending along the distal portion. The combination also includes a lock member threaded through the aperture and engaged with the release member; wherein the lock member restricts longitudinal and/or rotational movement of the stent frame with respect to the distal portion of the delivery device when the stent frame is in both of the compressed arrangement and the expanded arrangement until release of the lock member from the release member. In some embodiments, the lock member is wrapped one or more times around the release member. The release member can be selected from the group consisting of an elongate release pin and an elongate flexible member. In some embodiments, the distal portion of the delivery device includes a boss through which the release member is slidably positioned. In some embodiments, the boss is arranged orthogonal to the distal portion. In some embodiments, the lock member is threaded around and around the release member. In some embodiments, the lock member is a flexible loop of material. In some embodiments, the lock member is threaded through the distal portion. In some embodiments, the combination further includes a plurality of elongate tension members wrapped around a circumference of the stent frame to secure the stented prosthesis to the distal portion of the delivery device. In some embodiments, one transition element having a rounded surface is provided proximate each of the tension members at a location where each of the plurality of tension members changes direction.

The embodiments disclosed herein can be used in a method comprising providing a combination including: a stented prosthesis including a stent frame having a compressed arrangement and an expanded arrangement; wherein the stent frame includes a distal end and a proximal end and an aperture provided at one or more ends, e.g., the distal end; providing a delivery device including a distal portion on which the stented prosthesis is loaded in the compressed arrangement; the delivery device further including a release member extending along the distal portion; and a lock member threaded through the aperture. The method further includes delivering the stented prosthesis to a target site and disengaging the release member from the lock member to unlock the lock member so that the stent frame can move longitudinally and/or rotationally with respect to the distal portion of the delivery device in the compressed arrangement. The method can further include transitioning the stent frame from the compressed arrangement to the expanded arrangement; wherein a plurality of tension members compress the stented prosthesis during the step of delivering the stented prosthesis and the step of expanding the stented prosthesis includes releasing tension in the plurality of tension members. In some embodiments, one transition element having a rounded surface is provided proximate each of the tension members at a location where each of the plurality of tension members changes direction. In some embodiments, the transition element forms a lumen exterior to the distal portion of the delivery device. In some embodiments, the distal portion of the delivery device includes a boss through which the release member is slidably positioned. In some embodiments, the boss is arranged orthogonal to the distal portion of the delivery device. In some embodiments, the lock member is wrapped around and around the release member during the step of delivering the stented prosthesis to the target site. In some embodiments, the lock member is a flexible loop of material. In some embodiments, the lock member is threaded through the distal portion of the delivery device.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthesis to a target site, the delivery device comprising:

a distal portion configured to retain the stented prosthesis, the distal portion comprising a plurality of tiers extending along a length of the distal portion, the plurality of tiers comprising a first tier comprising a first length and a first lumen extending along the first length to a first distal aperture, the first lumen defined by a circumferential wall of the first tier surrounding an axis of the first tier, a second tier comprising a second length and a second lumen extending along the second length to a second distal aperture, the second tier comprising a second wall at least partially defining the second lumen, and the second wall of the second tier contacts and is attached to the circumferential wall of the first tier along the second length, wherein the second length is less than the first length such that the second distal aperture is proximally spaced from the first distal aperture to stagger the first distal aperture and the second distal aperture along the length of the distal portion, and wherein the plurality of tiers comprises a third tier comprising a third length and a third lumen extending along the third length to a third distal aperture, wherein the third length is less than the second length such that third distal aperture is proximally spaced from the second distal aperture to stagger the first distal aperture, the second distal aperture, and the third distal aperture along the length of the distal portion.

2. The delivery device of claim 1, further comprising a first elongate tension member at least partially extending through the first lumen and exiting the first distal aperture, wherein the first elongate tension member is configured to wrap around the stented prosthesis at a first axial location along a length of the stented prosthesis.

3. The delivery device of claim 2, further comprising a second elongate tension member at least partially extending through the second lumen and exiting the second distal aperture, wherein the second elongate tension member is configured to wrap around the stented prosthesis at a second axial location along the length of the stented prosthesis that is proximally spaced from the first axial location.

4. The delivery device of claim 1, wherein the first lumen is parallel to the second lumen.

5. The delivery device of claim 1, further comprising:

a first elongate tension member at least partially extending through the first lumen and exiting the first distal aperture, wherein the first elongate tension member is configured to wrap around the stented prosthesis at a first axial location along a length of the stented prosthesis;

a second elongate tension member at least partially extending through the second lumen and exiting the second distal aperture, wherein the second elongate tension member is configured to wrap around the stented prosthesis at a second axial location along the length of the stented prosthesis that is proximally spaced from the first axial location; and a third elongate tension member at least partially extending through the third lumen and exiting the third distal aperture, wherein the third elongate tension member is configured to wrap around the stented prosthesis at a third axial location along the length of the stented prosthesis that is proximally spaced from the second axial location.

6. The delivery device of claim 1, wherein the third lumen is parallel to the first lumen and the second lumen.

7. The delivery device of claim 1, wherein the first distal aperture, the second distal aperture, and the third distal aperture are circumferentially disposed relative to one another.

8. The delivery device of claim 1, wherein the third tier comprises a third wall at least partially defining the third lumen, and the third wall of the third tier contacts and is attached to the circumferential wall of the first tier along the third length.

9. The delivery device of claim 8, wherein the attachment of the second wall of the second tier to the circumferential wall of the first tier defines the second lumen between a portion of an outer circumferential surface of the circumferential wall of the first tier and an inner surface of the second wall of the second tier along a second axis of the second tier, and wherein the attachment of the third wall of the third tier to the circumferential wall of the first tier defines the third lumen between another portion of the outer circumferential surface of the circumferential wall of the first tier and an inner surface of the third wall of the third tier along a third axis of the third tier.

10. A delivery device for delivering a stented prosthesis to a target site, the delivery device comprising:

a distal portion configured to retain the stented prosthesis, the distal portion comprising a plurality of tiers extending along a length of the distal portion, the plurality of tiers comprising a first tier comprising a first length and a first lumen extending along the first length to a first distal aperture, the first lumen defined by a circumferential wall of the first tier surrounding an axis of the first tier, a second tier comprising a second length and a second lumen extending along the second length to a second distal aperture, the second tier comprising a second wall at least partially defining the second lumen, and the second wall of the second tier contacts and is attached to the circumferential wall of the first tier along the second length, wherein the second length is less than the first length such that the second distal aperture is proximally spaced from the first distal aperture to stagger the first distal aperture and the second distal aperture along the length of the distal portion, and wherein the attachment of the second wall of the second tier to the circumferential wall of the first tier defines the second lumen between a portion of an outer circumferential surface of the circumferential wall of the first tier and an inner surface of the second wall of the second tier along a second axis of the second tier.

* * * * *